(12) United States Patent
Hong et al.

(10) Patent No.: US 12,020,821 B2
(45) Date of Patent: Jun. 25, 2024

(54) METHOD AND APPARATUS OF PREDICTING FRACTURE RISK

(71) Applicant: INDUSTRY-ACADEMIC COOPERATION FOUNDATION, YONSEI UNIVERSITY, Seoul (KR)

(72) Inventors: Namki Hong, Seoul (KR); Yumie Rhee, Seoul (KR); Hea-jeong Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 349 days.

(21) Appl. No.: 17/539,434

(22) Filed: Dec. 1, 2021

(65) Prior Publication Data
US 2022/0208384 A1  Jun. 30, 2022

(30) Foreign Application Priority Data
Dec. 24, 2020 (KR) .......................... 10-2020-0182821

(51) Int. Cl.
*G16H 50/30* (2018.01)
*G06N 20/10* (2019.01)
(Continued)

(52) U.S. Cl.
CPC ............. *G16H 50/30* (2018.01); *G06N 20/10* (2019.01); *G06N 20/20* (2019.01); *G06T 5/20* (2013.01);
(Continued)

(58) Field of Classification Search
CPC ........ G16H 50/30; G16H 30/40; G16H 50/70; G16H 50/50; G16H 30/20; G16H 50/20; G06N 20/10; G06N 20/20; G06N 5/01; G06T 5/20; G06T 5/40; G06T 7/0012; G06T 7/40; G06T 11/001; G06T 2207/10116; G06T 2207/20081;
(Continued)

(56) References Cited

U.S. PATENT DOCUMENTS 6,385,283 B1 *  5/2002  Stein .................... A61B 6/505
                                                   378/174
10,588,589 B2 *  3/2020  Bregman-Amitai ..... G06N 5/02
(Continued)

FOREIGN PATENT DOCUMENTS

KR  10-2017-0034381 A  3/2017
KR  10-2020-0085470 A  7/2020

*Primary Examiner* — Michael S Osinski
(74) *Attorney, Agent, or Firm* — Hauptman Ham, LLP

(57) ABSTRACT

Embodiments of the present invention relate to methods of predicting fracture risk, which improve fracture risk prediction by developing a bone radiomics score model based on machine learning. As an embodiment of the present invention, the method of predicting the fracture risk is configured to perform the steps of designing a development set, processing bone images for a plurality of subjects included in the development set, extracting texture features from the bone images, selecting optimal texture features required to predict the fracture risk from the extracted texture features, performing machine learning for the optimal texture features using a training set of the development set, and designing a bone radiomics score model to predict the fracture risk.

16 Claims, 12 Drawing Sheets

(51) Int. Cl.

| | |
|---|---|
| *G06N 20/20* | (2019.01) |
| *G06T 5/20* | (2006.01) |
| *G06T 5/40* | (2006.01) |
| *G06T 7/00* | (2017.01) |
| *G06T 7/40* | (2017.01) |
| *G06T 11/00* | (2006.01) |
| *G06V 10/25* | (2022.01) |
| *G06V 10/54* | (2022.01) |
| *G16H 30/40* | (2018.01) |
| *G16H 50/70* | (2018.01) |

(52) U.S. Cl.
 CPC .............. *G06T 5/40* (2013.01); *G06T 7/0012* (2013.01); *G06T 7/40* (2013.01); *G06T 11/001* (2013.01); *G06V 10/25* (2022.01); *G06V 10/54* (2022.01); *G16H 30/40* (2018.01); *G16H 50/70* (2018.01); *G06T 2207/10116* (2013.01); *G06T 2207/20081* (2013.01); *G06T 2207/30008* (2013.01); *G06V 2201/033* (2022.01)

(58) Field of Classification Search
 CPC ... G06T 2207/30008; G06T 5/70; G06T 7/11; G06T 2207/20032; G06V 10/25; G06V 10/54; G06V 2201/033; G06V 2201/03; A61B 5/4504; A61B 5/4528
 See application file for complete search history.

(56) References Cited

U.S. PATENT DOCUMENTS

| | | | | |
|---|---|---|---|---|
| 10,622,102 | B2 * | 4/2020 | Itu | G16H 30/40 |
| 10,646,156 | B1 * | 5/2020 | Schnorr | G16H 30/40 |
| 10,716,529 | B2 * | 7/2020 | Bregman-Amitai | A61B 6/032 |
| 11,177,041 | B1 * | 11/2021 | Sutton | G16H 50/70 |
| 11,202,602 | B2 * | 12/2021 | Rajapakse | G16H 30/40 |
| 11,854,676 | B2 * | 12/2023 | Kalia | G16H 50/30 |
| 11,880,980 | B2 * | 1/2024 | Linguraru | G06T 7/40 |
| 2005/0148860 | A1 * | 7/2005 | Liew | G06T 7/0012 600/410 |
| 2007/0274442 | A1 * | 11/2007 | Gregory | A61B 6/482 600/407 |
| 2008/0058613 | A1 * | 3/2008 | Lang | G06T 7/0012 600/300 |
| 2010/0310141 | A1 * | 12/2010 | Wilson | A61B 6/482 600/300 |
| 2016/0015347 | A1 * | 1/2016 | Bregman-Amitai | G06T 7/0012 382/131 |
| 2016/0063720 | A1 * | 3/2016 | Han | G06F 18/2411 382/131 |
| 2018/0225823 | A1 * | 8/2018 | Zhou | G06T 7/11 |
| 2018/0247020 | A1 * | 8/2018 | Itu | G16H 10/60 |
| 2019/0236779 | A1 * | 8/2019 | Hattori | G01N 15/00 |
| 2019/0311805 | A1 * | 10/2019 | Linguraru | G06T 7/155 |
| 2019/0318828 | A1 * | 10/2019 | Li | G16H 30/40 |
| 2019/0340753 | A1 * | 11/2019 | Brestel | G16H 15/00 |
| 2019/0392547 | A1 * | 12/2019 | Katouzian | G06V 20/62 |
| 2020/0020097 | A1 * | 1/2020 | Do | G06F 18/2413 |
| 2020/0167911 | A1 * | 5/2020 | Park | G06T 7/11 |
| 2020/0219609 | A1 * | 7/2020 | Harte | G16H 30/40 |
| 2020/0265579 | A1 * | 8/2020 | Schmidt-Richberg | G16H 50/20 |
| 2021/0015421 | A1 * | 1/2021 | Cicero | G16H 30/20 |
| 2021/0082184 | A1 * | 3/2021 | Claessen | A61B 6/51 |
| 2021/0346091 | A1 * | 11/2021 | Haslam | G16H 30/40 |
| 2021/0350176 | A1 * | 11/2021 | Klaiman | G16H 30/40 |
| 2022/0037024 | A1 * | 2/2022 | Yoo | G06N 20/00 |
| 2022/0093268 | A1 * | 3/2022 | Li | G16H 10/60 |
| 2022/0198230 | A1 * | 6/2022 | Chen | G06F 18/2415 |
| 2023/0039451 | A1 * | 2/2023 | Lee | G16H 40/20 |
| 2023/0134785 | A1 * | 5/2023 | Stein | G06T 7/0012 382/131 |
| 2023/0215576 | A1 * | 7/2023 | Loupy | G16H 50/30 702/19 |
| 2023/0417851 | A1 * | 12/2023 | El-Baz | G01R 33/5608 |
| 2024/0037731 | A1 * | 2/2024 | Thomson | G06T 7/0012 |

\* cited by examiner

METHOD AND APPARATUS OF PREDICTING FRACTURE RISK

CROSS-REFERENCE TO RELATED APPLICATIONS

This application is based on and claims priority under 35 U.S.C. § 119 to Korean Patent Application No. 10-2020-0182821, filed on Dec. 24, 2020, in the Korean Intellectual Property Office, the disclosure of which is herein incorporated by reference in its entirety.

TECHNICAL FIELD

The present invention relates to a method of predicting fracture risk, and more particularly, to provide improved prediction performance for fracture risk by developing a bone radiomics score model based on machine learning.

BACKGROUND ART

Hip fracture becomes significant health problem in the era of global aging. The hip fracture may increase mortality, morbidity and economic burden. Currently, a method of measuring areal bone mineral density (aBMD) using dual energy X-ray absorptiometry (DXA) is a standard method for diagnosing osteoporosis. However, fragility fractures are caused in about half of individuals without osteoporosis determined by the method of measuring bone mineral density using only the DXA. Therefore, there is a need for a method of improving fracture risk prediction method.

PRIOR ARTS

Patent Document

1. Korean Patent Publication No. 2020-0085470: AI BONE DENSITY READING DEVICE AND METHOD
2. Korean Patent Publication No. 10-2017-0034381: COMPOSITIONS AND METHODS FOR MANAGING OR IMPROVING BONE DISORDERS, CARTILAGE DISORDERS, OR BOTH

DISCLOSURE

Technical Problem

An object of the present invention is to provide a method of predicting fracture risk related to a possibility that fracture occurs in the future.

Another object of the present invention is to provide a bone radiomics score model based on machine learning for fracture risk prediction.

Yet another object of the present invention is to provide a method of finding an optimal machine learning model for fracture risk prediction when a plurality of machine learning models are used.

Still another object of the present invention is to provide a method of estimating a bone radiomics score from bone images captured by dual energy X-ray absorptiometry (DXA).

Still yet another object of the present invention is to improve a method for hip fracture risk prediction by deriving texture features of a substrate for a region of interest from images and applying a learning machine thereto.

The technical objects of the present invention are not limited to those mentioned above, and other technical objects that are not mentioned may be considered by those skilled in the art to which the present invention pertains from embodiments of the present invention to be described below.

Technical Solution

Hereinafter, embodiments of the present invention relate to a method for predicting fracture risk, and to improve fracture risk prediction by developing a bone radiomics score model based on machine learning.

The bone radiomics score is a score system presented so as to predict fracture risk using optimal substrate features selected from texture features of a substrate obtained from bone images and has scores of 0 to 100 obtained by calculating a possibility of fracture from a machine learning model showing optimal performance in a test set.

According to an aspect of the present invention, a method of predicting fracture risk is configured to perform the steps of providing a development set, processing bone images for a plurality of subjects included in the development set, extracting texture features from the bone images, selecting optimal texture features required to predict the fracture risk from the extracted texture features, performing machine learning for the optimal texture features using a training set of the development set, and defining a bone radiomics score model to predict the fracture risk.

The machine learning may be performed using one of a random forest model, an elastic net model, a gradient boosting decision tree model, and a support vector machine model.

In the step of performing the machine learning, the machine learning may be performed by applying the optimal texture features to the random forest model, the elastic net model, the gradient boosting decision tree model, and the support vector machine model, respectively, and one machine learning model may be selected by evaluation result for each machine learning in the validation set. At this time, some of the training sets may be used as performance evaluation data to evaluate the performance of the bone radiomics score model.

According to another aspect of the present invention, there is provided to predict hip fracture risk through a bone radiomics score based on texture features of a substrate in regions of interest selected from a hip region.

To this end, the bone images may be a dual energy X-ray absorptiometry (DXA) hip images, four regions of interest corresponding to femoral neck, trochanter, intertochanter, and total hip may be configured from the DXA hip images, and wherein in the step of processing bone images, a preprocessing process for extracting texture features may be performed with respect to the four regions of interest.

The preprocessing process may be performed by a process of masking the regions of interest in different colors for each region along generated guidance lines, removing the guidance lines, and then improving substrate patterns through contrast-limited adaptive histogram equalization and median filtering.

At this time, the development set may be provided as a development set in which the case group and the control group are matched at 1:A from the case group data base and the control group data base. At this time, A may be selected from natural numbers other than 0.

The final development set may be provided by removing unusable bone images from the matched development set.

The optimal texture features may be GLRLM (Gray Level Run Length Matrix) Run Entropy, GLRLM GLNN (Gray Level Non-uniformity Normalized), GLCM (Grey Level Co-occurrence Matrix) IMC1 (Information Measure of Correlation 1), GLCM IDMN (Inverse Difference Moment Normalized), GLCM Cluster Prominence, GLSZM SZN (Size-Zone Non-Uniformity), GLSZM (Gray Level Size Zone Matrix) SAHGLE (Small Area High Gray Level Emphasis), GLSZM (Gray Level Size Zone Matrix) GLN (Gray Level Non-Uniformity), GLSZM GLV (Gray Level Variance), and GLDM (Gray Level Dependence Matrix) DNN (Dependence Non-Uniformity Normalized).

The bone image may be a dual energy X-ray absorptiometry (DXA) image. The embodiments and the computer program codes of the present invention may be configured to further perform a step of predicting the DXA image to be tested as a high-risk group when the bone radiomics score is more than a predetermined threshold, as a step of predicting whether there is fracture risk or the degree of fracture risk using the bone radiomics score model.

The aspects of the present invention described above are only some of preferred embodiments of the present invention, and it will be understood that various embodiments reflecting the technical features of the present invention may be derived based on the detailed description of the present invention to be described below by those skilled in the art.

Advantageous Effects

According to embodiments of the present invention, the following effects can be obtained.

According to the embodiments of the present invention, it is possible to provide an improved prediction method for fracture risk.

By providing the fracture risk prediction method based on machine learning, it is possible to predict more accurately the fracture even though reading only images.

It is possible to provide a method of finding an optimal machine learning model for fracture risk prediction when a plurality of machine learning models is used. For example, machine learning methods to be applied for each target bone may be varied, and it is possible to provide machine learning methods suitable for each subject.

It is possible to estimate whether there is fracture risk of a corresponding bone from bone images captured by dual energy X-ray absorptiometry (DXA) using a bone radiomics score model.

Particularly, according to the embodiments of the present invention, it is possible to accurately predict the risk of hip fracture through a bone radiomics score based on texture features in a region of interest selected in a hip region and to provide an effective assistant index to determine the hip fracture risk by medical staffs with the lack of clinical experience.

Effects which can be obtained in the present invention are not limited to the aforementioned effects and other unmentioned effects will be clearly understood by those skilled in the art from the following description. That is, unintentional effects according to the present invention can also be derived by those skilled in the art from the embodiments of the present invention.

DESCRIPTION OF DRAWINGS

In order to help the understanding of the present invention, the present invention is included as part of the detailed description, and the accompanying drawings provide various embodiments of the present invention. In addition, the accompanying drawings are also used to illustrate embodiments of the present invention together with the detailed description.

MODES FOR THE INVENTION

Figure 1:
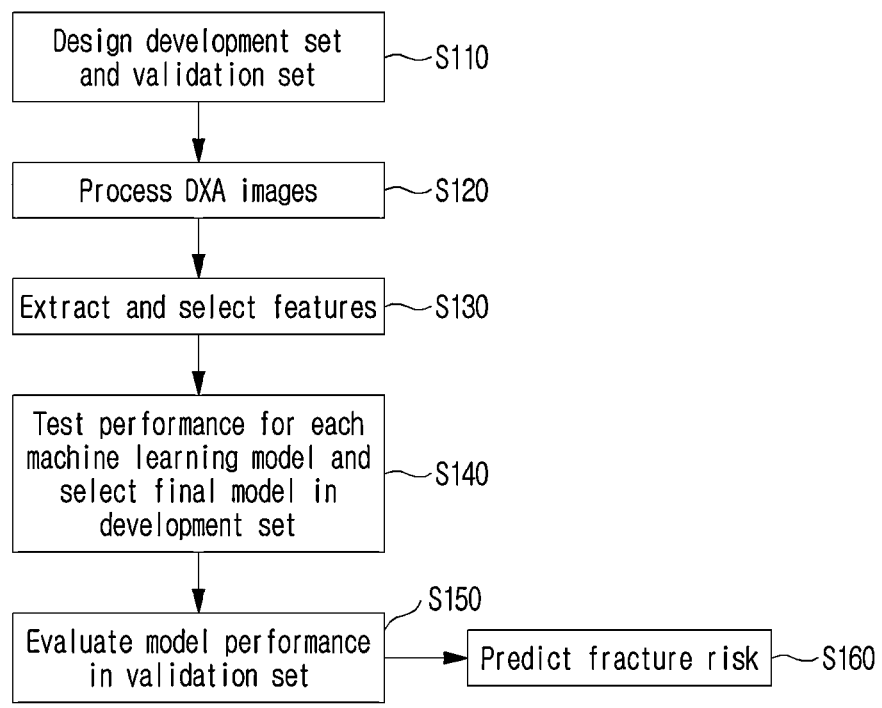
FIG. 1 is a diagram for describing a method for predicting fracture risk as an embodiment of the present invention.

The following embodiments are to combine components and features of the present invention in a predetermined form. Each component or feature should be considered as an option unless otherwise expressly stated. Each component or feature may be implemented not to be associated with other components or features. Further, the embodiment of the present invention may be configured by associating some components and/or features. The order of the operations described in the embodiments of the present invention may be changed. Some components or features of any embodiment may be included in another embodiment or replaced with the component and the feature corresponding to another embodiment.

In the description of the drawings, parts, devices, and/or configurations which may blur the gist of the present invention are not described, and parts, devices, and/or configurations enough to be understood by those skilled in the art had not been described. Further, parts designated by using the same reference numerals in the drawing mean the same components or steps in a device configuration or method.

Throughout the specification, unless explicitly described to the contrary, the word "comprise" and variations such as "comprises" or "comprising", will be understood to imply the inclusion of stated elements but not the exclusion of any other elements. In addition, the term "unit" or "er" as described in the specification refers to a unit for processing at least one function or operation. In addition, "a or an", "one", "the", and similar related words may be used as the meaning including both singular and plural forms, unless otherwise indicated in this specification or clearly refuted by the context, in the contexts of describing the present invention (especially, in the context of the following claims).

In addition, specific terms and/or symbols used in the embodiments of the present invention will be provided to help the understanding of the present invention, and the use of these specific terms may be changed to other forms without departing from the technical spirit of the present invention.

For example, the term of a texture feature of a substrate may be simply used as terms of a feature variable, a substrate feature, and a texture feature, and a case group may be used as the same meaning as a patient group.

Hereinafter, preferred exemplary embodiments of the present invention will be described in detail with reference to the accompanying drawings. The detailed description to be disclosed below in conjunction with the accompanying drawings is intended to illustrate exemplary embodiments of the present invention, and is not intended to represent only embodiments to be implemented in the present invention.

1. DXA and Radiomics

Dual energy X-ray absorptiometry (DXA) is a test of measuring bone mineral density by irradiating different types of X rays.

Radiomics is a method for comprehensive, automated high-throughput mining disease characteristics that are difficult to be identified with naked eyes as quantitative image features from standard-of-care medical imaging to support clinical decision with predictive performance or improved diagnostics.

The radiomics may quantify a large panel of radiologic phenotypes, including spatial and texture heterogeneity of the bone. Several studies based on bone histomorphometry, quantitative computed tomography (QCT), or plain X-ray images suggested substantial spatial heterogeneity related to aging and diseases in bone distribution and micro-architecture at proximal femur that may partially contribute to the fragility to hip fracture as well as bone mass alone. A recent study showed spatiotemporal heterogeneity in pixel-wise bone mineral density (BMD) with aging using unprocessed DXA hip images.

If properly used, the radiomics may be useful to mine texture indexes at pixel-wise level related to a hip fracture from DXA hip images, thereby more improving a method of predicting a hip fracture risk as add-on information to a DXA bone mineral density test in standard-of-care reference.

Hereinafter, a method of predicting the risk of fracture based on DXA and machine learning as embodiments of the present invention will be described.

2. Method for Fracture Risk Prediction Based on Machine Learning

The method of predicting the risk of fracture in embodiments of the present invention may be performed on all bones constituting the human body. However, hereinafter, there is disclosed a method of predicting the risk of fracture risk of the hip joint for convenience of explanation. In addition, a method of predicting the risk of fracture on bones of other sites may be performed in the same manner as the method of predicting the hip fracture risk.

FIG. 1 is a diagram for describing a method for predicting fracture risk as an embodiment of the present invention.

In embodiments of the present invention, a development set and a validation set may be designed for a method of predicting the risk of hip fracture based on DXA (S110).

First, a method of designing a development set will be described.

To develop a bone radiomics score model based on selected texture features which best discriminate individuals who sustain hip fracture or not, a development set, that is, a case-control study is designed.

The method of designing the development set will be described with reference to FIG. 2. Referring to a left side of FIG. 2, in the development set for the case-control study, samples are extracted from a case group data base 201 and samples are extracted from a control group data base 203 (S201 and S203). At this time, the 'case' or 'case group' means a patient group who sustained hip fracture. For example, in step S201, the case group may be configured as women aged 65 or older who sustained fragility hip fracture for an observation period.

The case group data base 201 may be an electronic health record (HER) data base. The EHR data base is a storage of information which stores patient's health information in the patient's consent for a predetermined period of time. The case group data base 201 may be called a case data base.

The control group data base 203 may be a Korean urban rural elderly (KURE) cohort data base. At this time, the control group may be configured as women aged 65 or older who did not sustain fragility hip fracture for an observation period. It may be assumed that DXA images for each sample are already stored in the EHR data base and/or the cohort data base.

The samples extracted from each data base are matched to 1:A (case group: control group). At this time, A may be a natural number of 2 or more as the number of samples (S205).

In step S205, a ratio of data samples may be appropriately determined according to a retained data set, and for example, the ratio may be set even at a ratio of M:N depending on the purpose of the fracture risk prediction method. At this time, M and N are natural numbers of 1 or more.

The matching development set configuration consists of a fracture patient group (or a case group) and a fracture-free control group (S207).

DXA bone images that are unusable in the matched development set may be removed. For example, in the matched development set, individuals without DXA hip images and individuals with DXA hip images which are unusable with different DXA machine types are removed from the matched development set (S209).

As a result, a final development set including the case group and the control group may be configured. 75% selected randomly from the final development set consists of a training set and the rest 25% consists of a test set. The training set is used for learning of machine learning to design the bone radiomics score model, and the test set is used for evaluating final performance on the bone radiomics score model learned through training (S211).

A DXA bone radiomics score model based on machine learning for fracture risk prediction may be designed using the final development set configured through step S211 (S213).

A more detailed method of designing the bone radiomics score model trained using the training set in the development set in steps S211 and S213 will be described below in relation to the remaining description of FIG. 1.

The validation set is to validate whether a model trained/learned to evaluate the performance of the designed bone radiomics score model is operated well. The validation set may be configured independently of the development set or may be configured using some of training sets of the final development set. In aspects of the present invention to be described below, it is assumed that the validation set is configured independently of the development set. However, according to a machine learning method, the validation set may be used as a validation set by sacrificing some of the training sets based on the development set. Only how to set a master sample of the validation set is just different, and functions as the validation set may be applied in the same manner.

control group may be configured as the case cohort group in addition to a sub-sampled control group and patients with hip fracture of a control group which is not sub-sampled. At this time, the sub-sampling ratio may vary depending on the purpose of fracture risk prediction, the size of the validation set and/or the study purpose.

The following Table 1 shows an example of the characteristics of the development set and the validation set.

TABLE 1

| | Development set (Case-control study: Hospital EHR and community cohort; median value of time to fracture: 2.1 [0.9-3.9] year) | | | Validation set (10% sub-sampling case - cohort study and community cohort) | | |
|---|---|---|---|---|---|---|
| | Case: Group that sustained hip fracture during follow-up period (n = 143) | Control group: Group that does not sustained hip fracture during follow-up period (n = 290) | P value | Group that sustained hip fracture during follow-up period (n = 34) | Group that does not sustained hip fracture during follow-up period (n = 186) | P value |
| Age | 73 ± 6 | 73 ± 6 | 0.807 | 75 ± 5 | 71 ± 4 | <0.001 |
| BMI | 23.2 ± 4.1 | 24.2 ± 3.1 | 0.004 | 23.6 ± 2.6 | 24.6 ± 3.0 | 0.091 |
| Previous fracture | 88 (62) | 97 (33) | <0.001 | 25 (73) | 58 (31) | <0.001 |
| DXA T-score | | | | | | |
| Lumbar spine | −2.1 ± 1.2 | −2.0 ± 1.2 | 0.477 | −1.9 ± 1.2 | −1.8 ± 1.1 | 0.713 |
| Femoral neck | −2.8 ± 1.0 | −2.2 ± 1.0 | <0.001 | −2.8 ± 0.9 | −2.0 ± 0.8 | <0.001 |
| Total hip | −2.0 ± 1.0 | −1.3 ± 1.0 | <0.001 | −2.0 ± 0.8 | −1.1 ± 0.8 | <0.001 |
| DXA osteoporosis | 98 (69) | 155 (53) | 0.003 | 26 (77) | 82 (44) | 0.001 |
| Previous anti-osteoporosis medication use | 31 (22) | 67 (23) | 0.739 | 9 (27) | 36 (19) | 0.344 |
| Diabetes | 46 (32) | 54 (19) | 0.002 | 8 (24) | 46 (25) | 0.881 |
| Hypertension | 93 (65) | 187 (64) | 0.910 | 26 (76) | 116 (62) | 0.114 |
| Any cancer | 16 (11) | 21 (7) | 0.167 | 4 (11.8) | 17 (9) | 0.632 |

A method of designing the validation set will be described with reference to a right side of FIG. 2 again. The validation set is used for a case-cohort study. To test the performance of the bone radiomics score model for the hip fracture risk prediction in a community-based cohort using a time-to-event data structure, the validation set is randomly sub-sampled using a case-cohort design of the KURE cohort.

When considering a labor-intensive and time-consuming characteristic of mask generation for the bone radiomics score model at a current stage, the case-cohort design provides an advantage that full covariate data are only needed on individual cases and subcohort, and may study multiple results unlike a nested case-control design which analyzes only a single result.

To design such a validation set, a master sample group is extracted from the control group data base 203 (S215).

Unnecessary control groups are removed from the extracted master sample group. At this time, the unnecessary control group means a sample group that does not fit the study purpose. For example, in the validation set for validating the bone radiomics score model designed for women aged 65 or older, a control group of men and a control group of women aged less than 65 are unnecessary. Therefore, it is preferred that these unnecessary control groups are removed (S217).

Thereafter, in the remaining sample groups, a control group is selected according to the purpose of the study for a follow-up period (S219), and a case cohort group is configured (S221).

In step S221, 10% of the control group may be sub-sampled to be configured as a case cohort group. 10% of the In Table 1, the data was denoted by a median value±standard deviation or probability (%). BMI is an abbreviation of body mass index, and EHR is an abbreviation of electronic health record. n refers to the number of the number of samples in each group.

The method of predicting fracture risk will be described with reference to FIG. 1 again.

Figure 2:
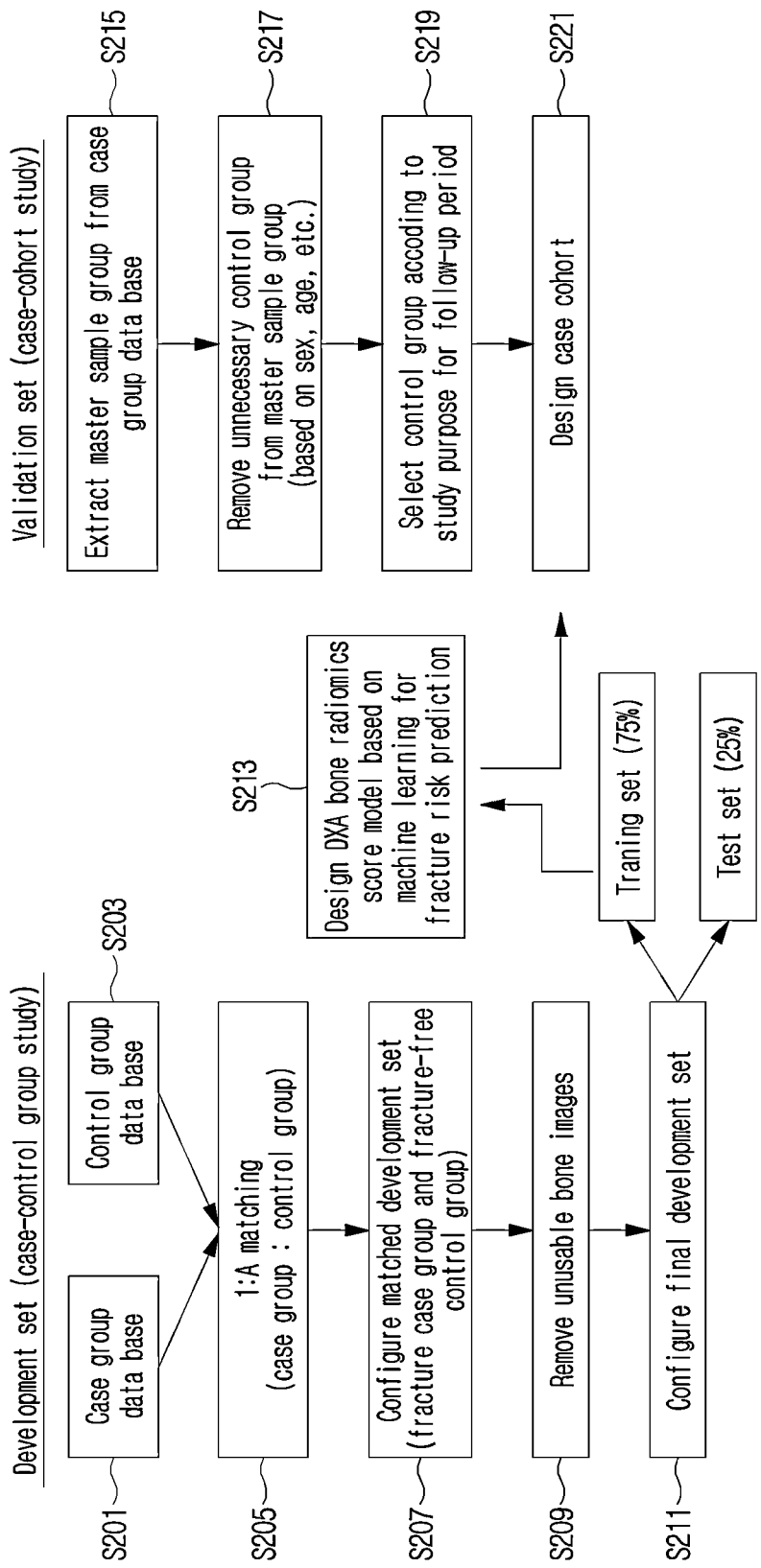
FIG. 2 is a diagram for describing a method of designing a development set and a validation set.

As described in S110 in FIG. 1 and in FIG. 2, the development set and the validation set may be designed. Thereafter, a process of processing DXA images for samples belonging to the training set is performed in the development set (S120).

Figure 3:
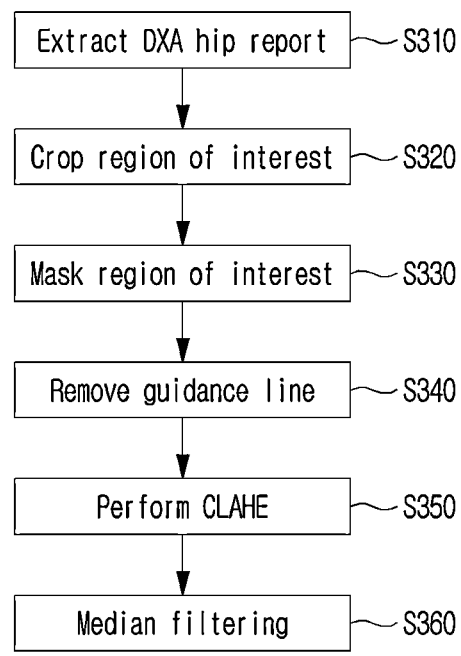
FIG. 3 is a diagram for describing a DXA image processing process.

In step S120, it is preferred that the DXA images are obtained in accordance with the standardized protocol of a predetermined institution. In step S120, the DXA image processing process is a preprocessing process for extracting substrate features, and will described below with reference to FIGS. 3 and 4.

DXA hip reports for samples in the training step may be extracted from a picture archival and communication system (PACS) or a picture data base. At this time, the DXA hip reports may be output to a digital imaging and communications in medicine (DICOM) file format (S310).

Figure 4:
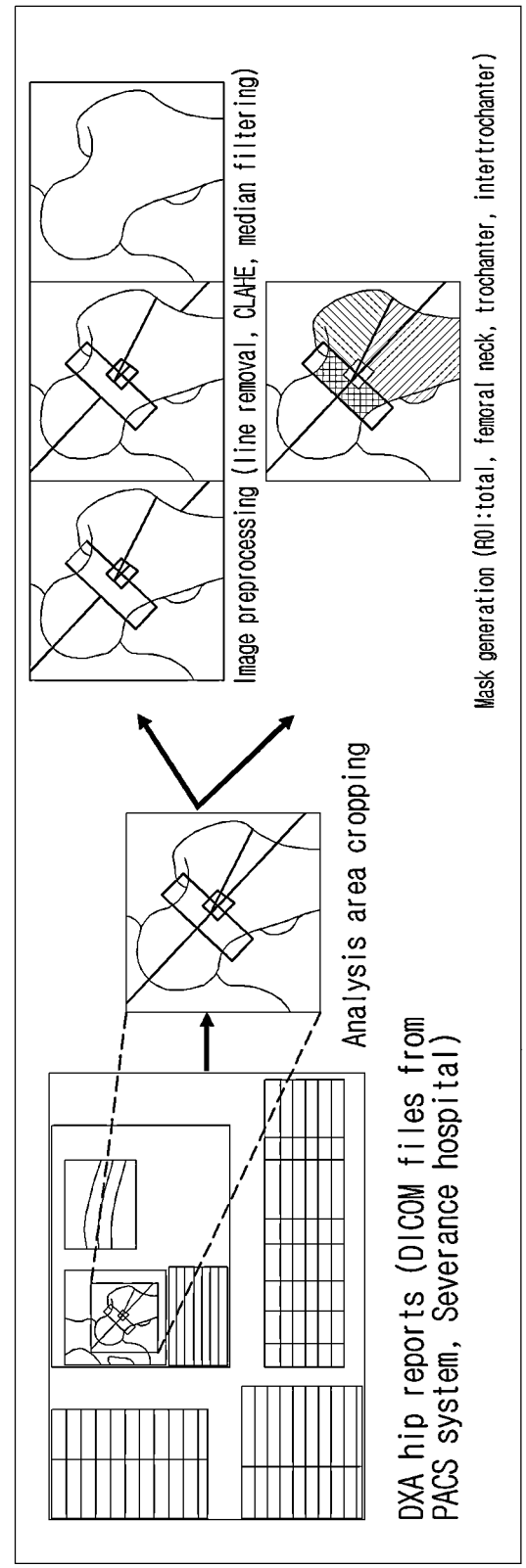
FIG. 4 is another diagram for describing a DXA image processing process.

The DXA hip report refers to DXA picture imaging data for the hip. In the output DXA hip image, cropping of analyzing a region of interest (ROI) to be analyzed through machine learning and trimming the picture images is performed. For example, a predetermined number of ROIs may be cropped in the proximal femur, which is an interest region in the hip region (S320). For example, the cropping may be achieved by selecting a region of interest in a square as illustrated in FIG. 4 and cropping the selected ROI.

In step S320, after cropping the ROI, a predetermined number of ROIs may be displayed in color, which is called masking. For example, when the ROIs are femoral neck, trochanter, intertochanter, and total hip, in the DXA images, masks with different colors may be generated for each region along guidance lines generated by a DXA machine so that the ROIs are distinguished (S330). As illustrated in FIG. 4, the masking operation is performed along guidance lines generated by the DXA machine and each ROI may be masked in a different color. The ROI may be set according to a type of bone to measure the fracture risk and may be set according to the use purpose of the user.

Thereafter, the guidance lines are removed (S340), a contrast-limited adaptive histogram equalization (CLAHE) step is performed (S350), and median filtering for reducing background noises in the DXA hip image and improving a texture (substrate) pattern is performed (S360). In particular, the median filtering process combined with the CLAHE step is performed to significantly contribute to improving the texture (substrate) pattern.

The method of predicting the fracture risk will be described with reference to FIG. 1 again.

In the DXA image processed in step S120 of FIG. 1, features for performing machine learning are extracted and selected (S130).

In step S130, texture features of a predetermined number of gray-level substrates are extracted in each of the ROIs in the DXA image. For example, in the case of using a pyradiomics program, up to 75 texture features may be automatically extracted for the ROIs in the DXA image. If the ROIs are four (e.g., femoral neck, trochanter, intertochanter, and total hip), 300 (75*4) texture features per one DXA image may be extracted.

75 texture features are texture features to analyze the hip fracture using the bone radiomics score model and may refer to Table 2 attached to the end of the detailed description.

Next, from the texture features extracted in step S130, texture features to be used in the bone radiomics score model based on machine learning for the facture risk prediction method are selected.

In this regard, Table 3 illustrates interclass correlation coefficients (ICCs) for 300 texture features obtained in four ROIs (Femoral neck; FN, Trochanter; TR, Intertochanter; IT, and Total Hip; TH) in 75 texture features in an automated process using pyradiomics 3.0, as a preferred embodiment of the present invention.

TABLE 3

('*' Mark: Extracted texture feature)

| Texture feature | Correlation in class (95% CI) | | | |
|---|---|---|---|---|
| | Total hip | Femoral neck | Intertochanter | Trochanter |
| Grey Level Co-occurrence Matrix (GLCM) features | | | | |
| Autocorrelation | 0.95 (0.90-0.97) | 0.97 (0.94-0.98) | 0.90 (0.79-0.95) | 0.91 (0.81-0.95) |
| Joint Average | 0.94 (0.88-0.97) | 0.97 (0.93-0.98) | 0.87 (0.73-0.93) | 0.90 (0.79-0.95) |
| Cluster Prominence | 0.99 (0.99-0.99) (*) | 0.99 (0.99-0.99) (*) | 0.99 (0.99-0.99) | 0.99 (0.99-0.99) |
| Cluster Shade | 0.99 (0.99-0.99) | 0.99 (0.99-0.99) | 0.99 (0.99-0.99) | 0.99 (0.99-0.99) |
| Cluster Tendency | 0.99 (0.99-0.99) | 0.99 (0.99-0.99) | 0.99 (0.99-0.99) | 0.99 (0.99-0.99) |
| Contrast | 0.99 (0.99-0.99) | 0.98 (0.97-0.99) | 0.99 (0.99-0.99) | 0.99 (0.99-0.99) |
| Correlation | 0.99 (0.99-0.99) | 0.99 (0.99-0.99) | 0.99 (0.99-0.99) | 0.99 (0.99-0.99) |
| Difference Average | 0.99 (0.99-0.99) | 0.99 (0.99-0.99) | 0.99 (0.99-0.99) | 0.99 (0.99-0.99) |
| Difference Entropy | 0.99 (0.99-0.99) | 0.99 (0.99-0.99) | 0.99 (0.99-0.99) | 0.99 (0.99-0.99) |
| Difference Variance | 0.99 (0.99-0.99) | 0.98 (0.97-0.99) | 0.99 (0.99-0.99) | 0.99 (0.99-0.99) |
| Joint Energy | 0.99 (0.99-0.99) | 0.99 (0.99-0.99) | 0.99 (0.99-0.99) | 0.99 (0.99-0.99) |
| Joint Entropy | 0.99 (0.99-0.99) | 0.99 (0.99-0.99) | 0.99 (0.99-0.99) | 0.99 (0.99-0.99) |
| Informational Measure of Correlation (IMC) 1 | 0.99 (0.99-0.99) (*) | 0.99 (0.99-0.99) (*) | 0.99 (0.99-0.99) | 0.99 (0.99-0.99) |
| Informational Measure of Correlation (IMC) 2 | 0.99 (0.99-0.99) | 0.99 (0.99-0.99) | 0.99 (0.99-0.99) | 0.99 (0.99-0.99) |
| Inverse Difference Moment (IDM) | 0.99 (0.99-0.99) | 0.99 (0.99-0.99) | 0.99 (0.99-0.99) | 0.99 (0.99-0.99) |
| MaximalCorrelation Coefficient (MCC) | 0.99 (0.99-0.99) | 0.99 (0.99-0.99) | 0.99 (0.99-0.99) | 0.99 (0.99-0.99) |
| Inverse Difference Moment Normalized (IDMN) | 0.98 (0.95-0.99) | 0.99 (0.98-0.99) (*) | 0.95 (0.90-0.98) (*) | 0.97 (0.94-0.99) |
| Inverse Difference (ID) | 0.99 (0.99-0.99) | 0.99 (0.99-0.99) | 0.99 (0.99-0.99) | 0.99 (0.99-0.99) |
| InverseDifference Normalized (IDN) | 0.98 (0.96-0.99) | 0.98 (0.97-0.99) | 0.96 (0.92-0.98) | 0.98 (0.96-0.99) |
| Inverse Variance | 0.99 (0.99-0.99) | 0.99 (0.99-0.99) | 0.99 (0.99-0.99) | 0.99 (0.99-0.99) |
| Maximum Probability | 0.99 (0.99-0.99) | 0.99 (0.99-0.99) | 0.99 (0.99-0.99) | 0.99 (0.99-0.99) |
| Sum Average | 0.94 (0.88-0.97) | 0.97 (0.93-0.98) | 0.87 (0.73-0.93) | 0.90 (0.79-0.95) |
| Sum Entropy | 0.99 (0.99-0.99) | 0.99 (0.99-0.99) | 0.99 (0.99-0.99) | 0.99 (0.99-0.99) |
| Sum of Squares | 0.99 (0.99-0.99) | 0.99 (0.99-0.99) | 0.99 (0.99-0.99) | 0.99 (0.99-0.99) |
| Gray Level Size Zone Matrix (GLSZM) features | | | | |
| Small Area Emphasis (SAE) | 0.88 (0.76-0.94) | 0.71 (0.40-0.86) | 0.82 (0.63-0.91) | 0.83 (0.65-0.92) |
| Large Area Emphasis (LAE) | 0.99 (0.99-0.99) | 0.98 (0.96-0.99) | 0.99 (0.99-0.99) | 0.98 (0.95-0.99) |
| Gray Level Non-Uniformity (GLN) | 0.98 (0.95-0.99) | 0.89 (0.78-0.95) | 0.98 (0.96-0.99) | 0.96 (0.93-0.98) (*) |
| Gray Level Non-Uniformity Normalized (GLNN) | 0.99 (0.98-0.99) | 0.97 (0.95-0.98) | 0.99 (0.98-0.99) | 0.96 (0.93-0.98) |
| Size-Zone Non-Uniformity (SZN) | 0.95 (0.90-0.97) | 0.96 (0.92-0.98) | 0.94 (0.87-0.97) | 0.72 (0.40-0.86) (*) |

TABLE 3-continued ('*' Mark: Extracted texture feature)

| Texture feature | Correlation in class (95% CI) | | | |
|---|---|---|---|---|
| | Total hip | Femoral neck | Intertochanter | Trochanter |
| Size-Zone Non-Uniformity Normalized (SZNN) | 0.92 (0.83-0.96) | 0.91 (0.81-0.95) | 0.88 (0.76-0.94) | 0.62 (0.20-0.82) |
| Zone Percentage (ZP) | 0.98 (0.97-0.99) | 0.97 (0.93-0.98) | 0.98 (0.97-0.99) | 0.97 (0.93-0.98) |
| Gray Level Variance (GLV) | 0.99 (0.99-0.99) | 0.98 (0.96-0.99) (*) | 0.99 (0.98-0.99) | 0.98 (0.97-0.99) |
| Zone Variance (ZV) | 0.99 (0.99-0.99) | 0.98 (0.96-0.99) | 0.99 (0.99-0.99) | 0.98 (0.96-0.99) |
| Zone Entropy (ZE) | 0.97 (0.95-0.98) | 0.96 (0.91-0.98) | 0.98 (0.97-0.99) | 0.95 (0.97-0.88) |
| Low Gray Level Zone Emphasis (LGLZE) | 0.88 (0.76-0.94) | 0.98 (0.95-0.99) | 0.81 (0.61-0.91) | 0.71 (0.40-0.86) |
| High Gray Level Zone Emphasis (HGLZE) | 0.96 (0.92-0.98) | 0.97 (0.95-0.98) | 0.94 (0.88-0.97) | 0.91 (0.81-0.95) |
| Small Area Low Gray Level Emphasis (SALGLE) | 0.91 (0.82-0.96) | 0.75 (0.48-0.88) | 0.88 (0.74-0.94) | 0.81 (0.61-0.91) |
| Small Area High Gray Level Emphasis (SAHGLE) | 0.90 (0.76-0.94) (*) | 0.92 (0.84-0.96) | 0.84 (0.67-0.92) | 0.80 (0.58-0.90) |
| Large Area Low Gray Level Emphasis (LALGLE) | 0.98 (0.97-0.99) | 0.98 (0.97-0.99) | 0.96 (0.93-0.98) | 0.95 (0.91-0.97) |
| Large Area High Gray Level Emphasis (LAHGLE) | 0.97 (0.94-0.98) | 0.97 (0.95-0.98) | 0.88 (0.75-0.94) | 0.94 (0.87-0.97) |
| Gray Level Run Length Matrix (GLRLM) features | | | | |
| Short Run Emphasis (SRE) | 0.99 (0.98-0.99) | 0.98 (0.96-0.99) | 0.99 (0.98-0.99) | 0.99 (0.98-0.99) |
| Long Run Emphasis (LRE) | 0.99 (0.99-0.99) | 0.99 (0.99-0.99) | 0.99 (0.99-0.99) | 0.99 (0.99-0.99) |
| Gray Level Non-Uniformity (GLN) | 0.99 (0.99-0.99) | 0.98 (0.97-0.99) | 0.99 (0.99-0.99) | 0.99 (0.98-0.99) |
| Gray Level Non-Uniformity Normalized (GLNN) | 0.99 (0.99-0.99) (*) | 0.99 (0.99-0.99) | 0.99 (0.99-0.99) | 0.99 (0.99-0.99) |
| RunLengthNon-Uniformity (RLN) | 0.99 (0.99-0.99) | 0.98 (0.97-0.99) | 0.99 (0.99-0.99) | 0.99 (0.99-0.99) |
| RunLengthNon-Uniformity Normalized (RLNN) | 0.99 (0.99-0.99) | 0.99 (0.99-0.99) | 0.99 (0.99-0.99) | 0.99 (0.99-0.99) |
| Run Percentage (RP) | 0.99 (0.99-0.99) | 0.99 (0.99-0.99) | 0.99 (0.99-0.99) | 0.99 (0.99-0.99) |
| Gray Level Variance (GLV) | 0.99 (0.99-0.99) | 0.99 (0.99-0.99) | 0.99 (0.99-0.99) | 0.99 (0.99-0.99) |
| Run Variance (RV) | 0.99 (0.99-0.99) | 0.99 (0.99-0.99) | 0.99 (0.99-0.99) | 0.99 (0.99-0.99) |
| Run Entropy (RE) | 0.99 (0.99-0.99) (*) | 0.99 (0.99-0.99) (*) | 0.99 (0.99-0.99) | 0.99 (0.99-0.99) |
| Low Gray Level Run Emphasis (LGLRE) | 0.92 (0.83-0.96) | 0.93 (0.86-0.97) | 0.74 (0.46-0.87) | 0.81 (0.60-0.91) |
| High Gray Level Run Emphasis (HGLRE) | 0.95 (0.90-0.97) | 0.97 (0.94-0.98) | 0.90 (0.80-0.95) | 0.90 (0.80-0.95) |
| Short Run Low Gray Level Emphasis (SRLGLE) | 0.90 (0.79-0.95) | 0.94 (0.89-0.97) | 0.75 (0.47-0.88) | 0.72 (0.42-0.86) |
| Short Run High Gray Level Emphasis (SRHGLE) | 0.97 (0.95-0.98) | 0.98 (0.96-0.99) | 0.95 (0.91-0.98) | 0.94 (0.88-0.97) |
| Long Run Low Gray Level Emphasis (LRLGLE) | 0.97 (0.95-0.99) | 0.98 (0.97-0.99) | 0.91 (0.82-0.95) | 0.96 (0.92-0.98) |
| Long Run High Gray Level Emphasis (LRHGLE) | 0.95 (0.90-0.97) | 0.96 (0.92-0.98) | 0.85 (0.70-0.93) | 0.89 (0.78-0.95) |
| Gray Level Dependence Matrix (GLDM) features | | | | |
| Small Dependence Emphasis (SDE) | 0.99 (0.98-0.99) | 0.97 (0.94-0.98) | 0.99 (0.98-0.99) | 0.97 (0.95-0.99) |
| Large Dependence Emphasis (LDE) | 0.99 (0.99-0.99) | 0.99 (0.99-0.99) | 0.99 (0.99-0.99) | 0.99 (0.99-0.99) |
| Gray Level Non-Uniformity (GLN) | 0.99 (0.99-0.99) | 0.99 (0.99-0.99) | 0.99 (0.99-0.99) | 0.99 (0.99-0.99) |
| Dependence Non-Uniformity (DN) | 0.99 (0.99-0.99) | 0.98 (0.97-0.99) | 0.99 (0.99-0.99) | 0.99 (0.99-0.99) |
| Dependence Non- Uniformity Normalized (DNN) | 0.99 (0.99-0.99) (*) | 0.99 (0.99-0.99) | 0.99 (0.99-0.99) | 0.99 (0.99-0.99) |
| Gray Level Variance (GLV) | 0.99 (0.99-0.99) | 0.99 (0.99-0.99) | 0.99 (0.99-0.99) | 0.99 (0.99-0.99) |
| Dependence Variance (DV) | 0.99 (0.99-0.99) | 0.97 (0.95-0.98) | 0.99 (0.98-0.99) | 0.98 (0.97-0.99) |
| Dependence Entropy (DE) | 0.99 (0.99-0.99) | 0.99 (0.99-0.99) | 0.99 (0.99-0.99) | 0.99 (0.99-0.99) |
| Low Gray Level Emphasis (LGLE) | 0.93 (0.86-0.96) | 0.92 (0.84-0.96) | 0.72 (0.41-0.86) | 0.90 (0.79-0.95) |
| High Gray Level Emphasis (HGLE) | 0.95 (0.90-0.97) | 0.97 (0.94-0.98) | 0.90 (0.79-0.95) | 0.91 (0.81-0.95) |
| Small Dependence Low Gray Level Emphasis (SDLGLE) | 0.91 (0.82-0.95) | 0.90 (0.79-0.95) | 0.70 (0.37-0.85) | 0.83 (0.65-0.92) |
| Small Dependence High Gray Level Emphasis (SDHGLE) | 0.96 (0.92-0.98) | 0.98 (0.96-0.99) | 0.94 (0.89-0.97) | 0.91 (0.82-0.96) |
| Large Dependence Low Gray Level Emphasis (LDLGLE) | 0.94 (0.88-0.97) | 0.94 (0.89-0.97) | 0.74 (0.46-0.87) | 0.92 (0.84-0.96) |
| Large Dependence High Gray Level Emphasis (LDHGLE) | 0.95 (0.89-0.97) | 0.97 (0.94-0.98) | 0.88 (0.74-0.94) | 0.90 (0.80-0.95) |

TABLE 3-continued ('*' Mark: Extracted texture feature)

| | Correlation in class (95% CI) | | | |
|---|---|---|---|---|
| Texture feature | Total hip | Femoral neck | Intertochanter | Trochanter |

Neighbouring Gray Tone DifferenceMatrix (NGTDM) features

| | | | | |
|---|---|---|---|---|
| Coarseness | 0.99 (0.99-0.99) | 0.98 (0.97-0.99) | 0.99 (0.99-0.99) | 0.99 (0.98-0.99) |
| Contrast | 0.98 (0.97-0.99) | 0.97 (0.93-0.98) | 0.97 (0.95-0.98) | 0.98 (0.97-0.99) |
| Busyness | 0.95 (0.90-0.97) | 0.97 (0.95-0.98) | 0.90 (0.80-0.95) | 0.90 (0.79-0.95) |
| Complexity | 0.99 (0.98-0.99) | 0.97 (0.95-0.98) | 0.97 (0.95-0.99) | 0.98 (0.96-0.99) |
| Strength | 0.99 (0.99-0.99) | 0.99 (0.98-0.99) | 0.99 (0.98-0.99) | 0.99 (0.98-0.99) |

A process for selecting the best texture feature for fracture risk prediction may be performed by 1) scaling the extracted texture features, 2) normalizing the scaled texture features, 3) removing highly correlated texture features (e.g., correlation coefficient >0.80) from the normalized texture features, 4) selecting significantly associated texture features (correction p value <0.20) after false discovery rate-based multiple analysis correction in univariate analysis, and 5) selecting a minimum important feature combination of maximizing F1 score through recursive feature elimination with cross validation from the selected texture features based on data.

Steps 1) to 5) for selecting the texture features described above are a process of selecting the features, and a selection process to select important features through mathematical algorithm models without selecting features with a subjective opinion of a particular person (or user). Through steps 1) to 5), features with high correlation (that is, a correlation coefficient is high) are removed and minimum important feature combination of maximizing the F1 score may be selected from the features based on the data through recursive feature elimination with cross validation.

Through the selection process, a predetermined number of optimal texture features are selected. For example, when it is assumed that 75 texture features are extracted in step S130, 14 texture features marked by (*) among texture features of Table 3 have been extracted through the above process.

To predict the fracture risk for women aged 65 or older that sustained hip fracture, 14 texture features may be selected. The selected 14 texture features may refer to FIG. 5.

Figure 5:
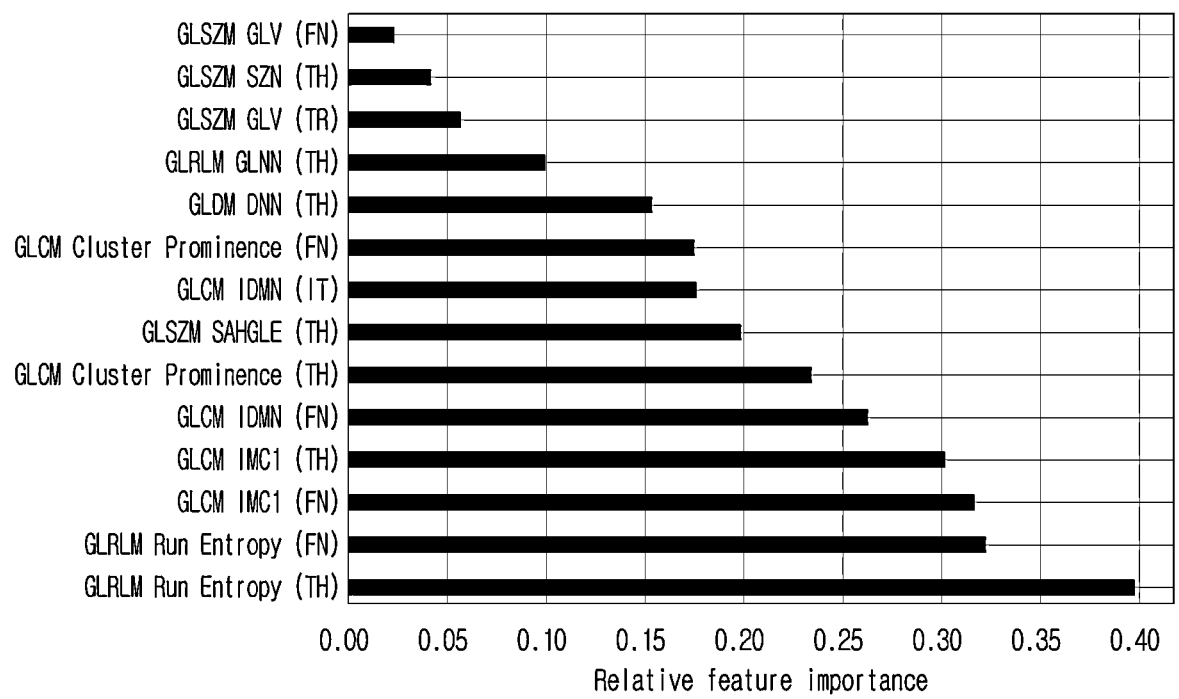
FIG. 5 is a diagram for describing a predetermined number of selected texture features.

Referring to FIG. 5, a vertical axis represents selected texture features, and a horizontal axis represents relative feature importance between the texture features. In FIG. 5, the importance of GLRLM Run Entropy (TH) is highest as 0.40 and GLSZM GLV (FN) has the importance of about 0.02 to 0.03.

Here, based on four ROIs, femoral neck (FN), trochanter (TR), intertochanter (IT), and total hip (TH), the selected texture features may be preferably 14 texture features of GLRLM (Gray Level Run Length Matrix) Run Entropy of total hip (TH), GLRLM (Gray Level Run Length Matrix) Run Entropy of femoral neck (FN), GLCM (Grey Level Co-occurrence Matrix) IMC1 (Information Measure of Correlation 1) of femoral neck (FN), GLCM (Grey Level Co-occurrence Matrix) IMC1 (Information Measure of Correlation 1) of total hip (TH), GLCM IDMN (Inverse Difference Moment Normalized) of femoral neck (FN), GLCM Cluster Prominence of total hip (TH), GLSZM (Gray Level Size Zone Matrix) SAHGLE (Small Area High Gray Level Emphasis) of total hip (TH), GLCM IDMN (inverse difference moment normalized) of intertochanter (IT), GLCM Cluster Prominence of femoral neck (FN), GLDM (Gray Level Dependence Matrix) DNN (Dependence Non-Uniformity Normalized) of total hip (TH), GLRLM GLNN (Gray Level Non-uniformity Normalized) of total hip (TH), GLSZM (Gray Level Size Zone Matrix) GLN (Gray Level Non-Uniformity) of trochanter (TR), GLSZM SZN(Size-Zone Non-Uniformity) of total hip (TH), and GLSZM GLV (Gray Level Variance) of femoral neck (FN).

The 14 texture features are employed to quantify texture patterns that are difficult to be certified with naked eye. In the shown patterns, in a fracture high-risk group, a difference in signal intensity between pixels is reduced (that is, a black and white difference is reduced) even in the same bone mineral density, while a pattern in which black and white pixels are arranged is further irregular.

Meanwhile, in people with low fracture risk, the difference in signal intensity between pixels is large even in the same bone mineral density, while a pattern arrangement between pixels is regular.

At this time, the Gray Level Run Length Matrix (GLRLM) quantifies a gray level run defined as a length of the number of pixels. In addition, the GLRLM Run entropy measures uncertainty and randomness for the distribution of gray level and run length. The GLRLM GLNN (Gray Level Non-Uniformity Normalized) is used to measure the similarity of gray level intensity values in the image.

In addition, the GLSZM (Gray Level Size Zone Matrix) may quantify a gray zone region in the DXA image. The GLSZM GLV (Gray level Variance) feature measures gray level luminance for these zones, the GLSZM GLN (Gray Level Non-Uniformity) measures variability of the gray level intensity value, and the GLSZM SZN(Size-Zone Non-Uniformity) measures variability of a size region in the image.

The GLSZM (Gray Level Size Zone Matrix) SAHGLE (Small Area High Gray Level Emphasis) represents a value of measuring a ratio in a joint distribution image of a smaller region with a higher gray level value.

The GLCM (Grey Level Co-occurrence Matrix) IMC1 (informal measure of correlation 1) represents a feature of texture of the image and the GLCM IDMN (Inverse Difference Moment Normalized) measures the homogeneity of the image. The GLCM Cluster Prominence represents a measurement value for GLCM distortion and asymmetry.

The GLDM (Gray Level Dependence Matrix) DNN (Dependence Non-Uniformity Normalized) is a value for measuring the similarity of dependencies throughout the image, and represents more homogeneity of the dependency as the value is lower.

The aforementioned texture features and the remaining texture features may refer to the description described in the following Table 2.

Referring back to FIG. 1, a machine learning model to be used in the radiomics score model for predicting hip fracture risk may be selected by testing performance for each machine learning model using the development set designed in step S110 (S140).

Machine learning models which may be used in a training set of the development set have about four types. For example, there are a random forest model, an elastic net model, a gradient boosting decision tree model, and a support vector machine model. Hyperparameters for each model are coordinated using a grid search method repeating 3-fold cross validation 5 times.

In the test set of the development set, the machine learning models are evaluated using indicators such as Area Under the Receiver-Operating characteristics Curve (AUROC) and Area Under the Precision-Recall Curve (AUPRC). The machine running model calibration is evaluated using a Brier Score that separates reliability (difference between prediction probabilities and true probabilities) and resolution (difference of conditional probabilities from predicted average).

In step S140, the performance evaluation and measurement results for each machine learning model for the DXA image in the development set are shown in Table 4 below. The following Table 4 shows the performance and measurement matrices of machine learning models for predicting hip fracture using texture features from hip DXA images.

TABLE 4

| Test set | Accuracy | Precision | Recall | F1-score | AUROC | AUPRC | Brier score |
| --- | --- | --- | --- | --- | --- | --- | --- |
| Random forest | 0.73 | 0.58 | 0.72 | 0.64 | 0.784 | 0.664 | 0.175 |
| GBDT | 0.72 | 0.61 | 0.47 | 0.53 | 0.768 | 0.638 | 0.180 |
| SVC | 0.74 | 0.59 | 0.72 | 0.65 | 0.759 | 0.607 | 0.182 |
| Elastic net | 0.73 | 0.56 | 0.86 | 0.62 | 0.758 | 0.607 | 0.182 |

In Table 1: GBDT is an abbreviation of gradient boosted decision tree, SVC is an abbreviation of support vector classifier, AUROC is an abbreviation of area under the receiver-operating characteristics curve, and AUPRC is an abbreviation of area under the precision-recall curve.

Referring to Table 4, Brier Score of four DXA hip radiomics models is in the range of 0.175 to 0.182, and the above models have similar accuracy. However, it can be seen that the values of AUROC and AUPRC showed best performance in the random forest model.

Therefore, the random forest model determined to have the best performance is selected to measure the bone radiomics score. That is, the 14 texture features selected in step S130 are used to train the random forest model.

Figure 6:
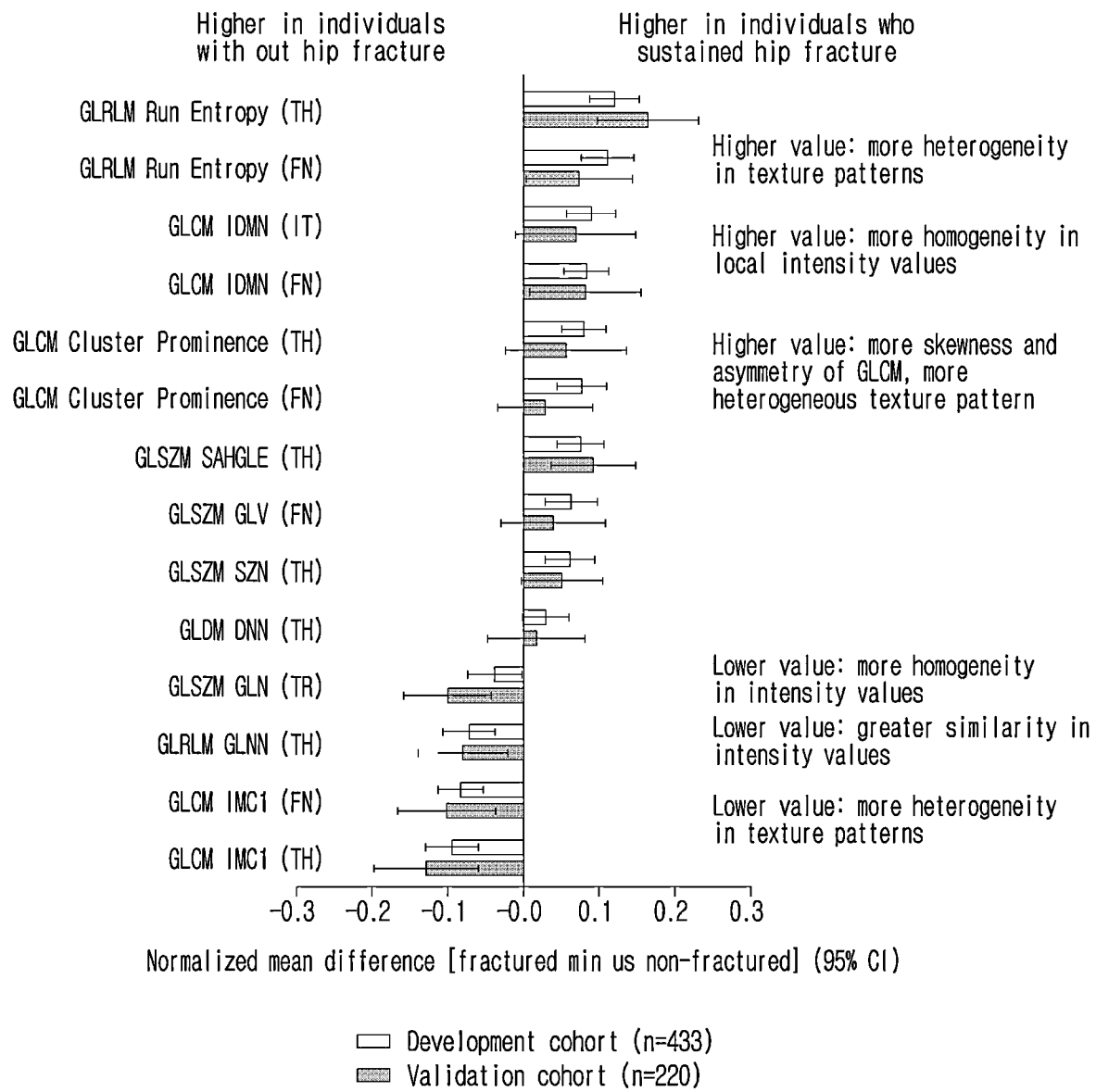
FIG. 6 illustrates a normalized mean difference of texture features selected in a final model between individuals who sustained hip fracture and individuals without hip fracture.

Among the 14 texture features, six texture features of GLRLM (Gray Level Run Length Matrix) Run Entropy of total hip (TH), GLRLM (Gray Level Run Length Matrix) Run Entropy of femoral neck (FN), GLCM (Grey Level Co-occurrence Matrix) IMC1 (Information Measure of Correlation 1) of femoral neck (FN), GLCM (Grey Level Co-occurrence Matrix) IMC1 (Information Measure of Correlation 1) of total hip (TH), GLCM IDMN (Inverse Difference Moment Normalized) of femoral neck (FN), and GLCM Cluster Prominence of total hip (TH), as illustrated in FIG. 5, may be treated as six texture features with high importance contributing to the random forest model. Referring to FIG. 6, individuals who sustained hip fracture showed higher GLRLM (Gray Level Run Length Matrix) Run Entropy and lower GLCM (Grey Level Co-occurrence Matrix) IMC1 (Information Measure of Correlation 1) in both the development set and the validation set than individuals without hip facture, and showed larger heterogeneity in both substrate patterns. Further, the individuals who sustained hip fracture showed higher GLCM IDMN (Inverse Difference Moment Normalized) and lower GLSZM (Gray Level Size Zone Matrix) GLN (Gray Level Non-Uniformity) in both the development set and the validation set than those without hip fracture and show a smaller deviation in both gray-level pixel intensity values.

The random forest model determined in the validation set designed in step S110 may be evaluated (S150).

In the validation set, when the performance of the models selected in step S140 is validated, the training for the fracture risk prediction is performed and used for actual prediction (S160).

Steps S140 and S150 described above may not be performed. For example, in the case of using many machine learning models, machine learning models may be selected based on the extracted texture features, but in the case of considering only one machine learning model, the corresponding steps may not be performed. However, even in this case, it is preferable that the performance evaluation of whether the corresponding machine learning model is suitable for the validation set is performed.

Figure 7A:
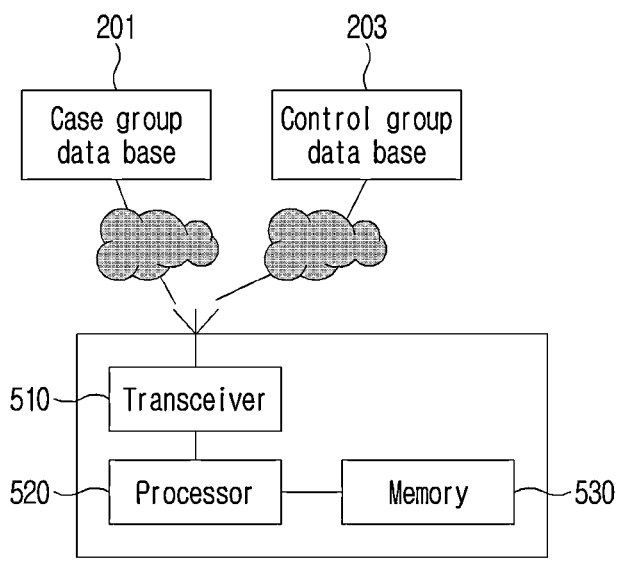
FIG. 7A is a diagram for describing a device and FIG. 7B is a computer recording medium in which the method for the fracture risk prediction described in FIGS. 1 to 6 may be performed.
Figure 7B:
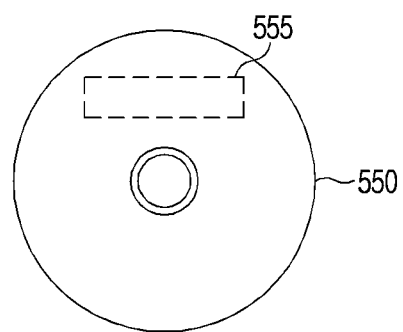

FIG. 7A is a diagram for describing a device and FIG. 7B is a computer recording medium in which the method for the fracture risk prediction described in FIGS. 1 to 6 may be performed.

FIG. 7A illustrates an example of a device structure in which the method of predicting the fracture risk is performed and FIG. 7B illustrates an example of a recording medium in which a program of predicting the fracture risk is recorded.

The device illustrated in FIG. 7A may include a transceiver 510 for wired/wireless communication, a processor 520 for controlling the device, and a memory 530. The transceiver 510 may perform communication with external or internal data bases wiredly and/or wirelessly. Through the communication, the transceiver 510 may receive and acquire DXA image data from the data bases. The processor controls the transceiver 520 and the memory 530, and may control the transceiver 520 to perform communication with the external or internal data bases using instructions stored in the memory 530. Further, the processor 520 may decode a DXA image file received by the transceiver and may perform the fracture risk prediction method described in FIGS. 1 to 6 by controlling the instructions stored in the memory.

In FIG. 7A, the transceiver 510 may perform wired or wireless communication with the case group data base 201 and the control group data base 203. The case group data base 201 and the control group data base 203 may be configured outside the device, but may be configured inside the device In FIG. 7B, a computer readable medium 550 including computer program codes 555 for predicting the fracture risk is configured to perform steps of designing a development set, processing bone images for a plurality of subjects included in the development set, extracting texture features from the bone images, selecting optimal texture features required to predict the fracture risk from the extracted texture features, performing machine learning for the optimal texture features using a training set of the development set, and designing a bone radiomics score model to predict the fracture risk, by the computer when the computer program codes are executed in the computer.

In FIG. 7B, the computer readable medium 550 has been illustrated in a compact disk (CD) shape, but is not limited thereto, and may be forms such as USB, DVD, flash memory, RAM, ROM, and the like. Further, the computer readable medium 550 may mean all storage media which may download and store the program codes 555 online. In addition, the computer program codes 555 may include a form that is downloaded in an application form in a portable terminal device such as a smartphone or a fixed terminal device.

The machine learning may be performed using one of a random forest model, an elastic net model, a gradient boosting decision tree model, and a support vector machine model.

In the step of performing the machine learning, the machine learning is performed by applying the optimal texture features to the random forest model, the elastic net model, the gradient boosting decision tree model, and the support vector machine model, respectively, and one machine learning model may be selected by applying the result to the validation set. At this time, some of the training sets may be used as performance evaluation data to evaluate the performance of the bone radiomics score model.

At this time, the development set may design a development set in which the case group and the control group are matched at 1:A from the case group data base and the control group data base. At this time, A may be selected from natural numbers other than 0.

The final development set may be designed by removing unusable bone images from the matched development set.

For example, the optimal texture features may include at least one of GLRLM (Gray Level Run Length Matrix) Run Entropy, GLRLM GLNN (Gray Level Non-uniformity Normalized), GLCM (Grey Level Co-occurrence Matrix) IMC1 (Information Measure of Correlation 1), GLCM IDMN (Inverse Difference Moment Normalized), GLCM Cluster Prominence, GLSZM SZN(Size-Zone Non-Uniformity), GLSZM (Gray Level Size Zone Matrix) SAHGLE (Small Area High Gray Level Emphasis), GLSZM (Gray Level Size Zone Matrix) GLN (Gray Level Non-Uniformity), GLSZM GLV (Gray Level Variance), and GLDM (Gray Level Dependence Matrix) DNN (Dependence Non-Uniformity Normalized), and each substrate feature may be extracted for each of a plurality of ROIs. The detailed description of the texture features may refer to Table 2. Further, preferably, as described above, 14 texture features selected according to the random forest model may be applied.

The bone image may be a dual energy X-ray absorptiometry (DXA) image. The embodiments and the computer program codes of the present invention may be configured to further perform a step of predicting whether there is fracture risk or the degree of fracture risk in the DXA image to be tested using the bone radiomics score model.

3. Example

Hereinafter, Examples of the embodiments of the present invention described in FIGS. 1 to 7 will be described.

In FIG. 2, the case group data base in the development set was EHR data base of Severance hospital. At this time, a case group consisted of women aged 65 or older and individuals who sustained fragility hip fracture for an observation period of January, 2010 and December, 2019. The number N of samples in the case group was 172.

The control group data base of the development set was KURE cohort data base, and the control group consisted of women aged 65 or older who did not sustain fragility hip fracture for an observation period of January, 2012 to December, 2018.

The case group and the control group were matched at a ratio of 1:2, and a follow-up period was 0.9 year to 3.9 years, and a median value was 2.1 years. The matched development set included 441 samples. At this time, the number of samples who sustained the hip fracture was 147 and the number of samples in the control group was 294.

Among them, samples without DXA hip images or those without reading DXA images due to a different DXA machine type have been excluded by 4 persons in the case group and 4 persons in the control group.

Accordingly, the final development set consisted of a total of 433 samples of 143 in the case group and 290 in the control group.

In the total samples, the training set for performing the machine learning for the DXA image was randomly selected 75% and the remaining 25% was configured as a test set to evaluate the performance.

In FIG. 2, the validation set was intended to evaluate the performance of DXA-based bone radiomics score model learned through machine learning. In the KURE cohort data base, a sample group was extracted from individuals who have been followed-up until Dec. 31, 2018 among individuals registered for 2012 to 2015. That is, the total samples were 3517.

At this time, since women aged 65 or older were targeted, 1163 men samples were excluded from the samples, and 294 women included in the matched control group were also excluded. Finally, 7 individuals without using the DXA hip images were excluded.

Accordingly, for a follow-up period of 4.5 to 5.7 years (median value of 5.4 years), women aged 65 or older which may be configured in the control group were 2053.

The case cohort may be set with 10% randomly subsampled control group. At this time, 10% subcohort consisted of 186 individuals without hip fracture and 3 individuals with hip fracture and in addition to the configured subcohort, 31 individuals who sustained the hip fracture was configured as the case cohort. Therefore, a case cohort with a total of 220 samples was designed.

Table 1 showed result values obtained based on the development set and the validation set configured in the above-described Example.

Table 4 showed result values of training and testing machine learning models suitable for configuring the bone radiomics score model for the fracture risk prediction method of the present invention based on the development set configured in the above-described Example.

To derive the corresponding results, 75 texture features shown in Table 2 were used and among them, the machine learning models were trained based on 14 optimal texture features, respectively.

3.1 Results

The following results will be described with reference to Table 1.

In a development set, a mean age of subjects was 73 years (case group 73±6 vs. control group 73±6, p=0.807), and an observation end time from a time of hip fracture or DXA testing was 2.1 years. A case group (the number of samples is 143) had significantly lower femoral neck T-score (−2.8±1.0 vs. −2.2±1.0, p<0.001) and more fragility fracture history (62% vs 33%, p<0.001) than a control group (n=290).

In a validation set, that is, a validation cohort (case-cohort), 34 subjects who sustained hip fracture during a follow-up period had older age (75±5 vs. 71±4 year, p<0.001), higher prevalence of previous fracture (73% vs 31%, p<0.001), DXA-defined osteoporosis (77% vs. 44%, p=0.001), and lower femoral neck T-score (−2.8±0.9 vs. −2.0±0.8, p<0.001) than those who did not sustain any hip fracture (n=186).

Correlation Between Clinical Parameters and Bone Radiomics Score

In the validation set and the validation cohort, a bone radiomics score ranged 12 to 74, with a mean score of 29 and a standard deviation of 13. The bone radiomics score showed a weak and modest correlation with age (r=0.13, p=0.049), height (r=0.18, p=0.009), femoral neck BMD (r=−0.31, p<0.001), total hip BMD (r=−0.30, p<0.001), and FRAX hip fracture probabilities (r=0.21, p=0.002). At this time, weight (r=−0.07, p=0.330) and lumbar spine BMD (r=0.029, p=0.671) had no correlation with the bone radiomics score. A higher bone radiomics score was observed in individuals who have previous fragility fracture history (32±15 vs. 27±12, p=0.012) or DXA-based osteoporosis (32±15 vs. 26±10, p<0.001) than those without these histories.

Hip Fracture Prediction Result Using Bone Radiomics Score Model

Figure 8:
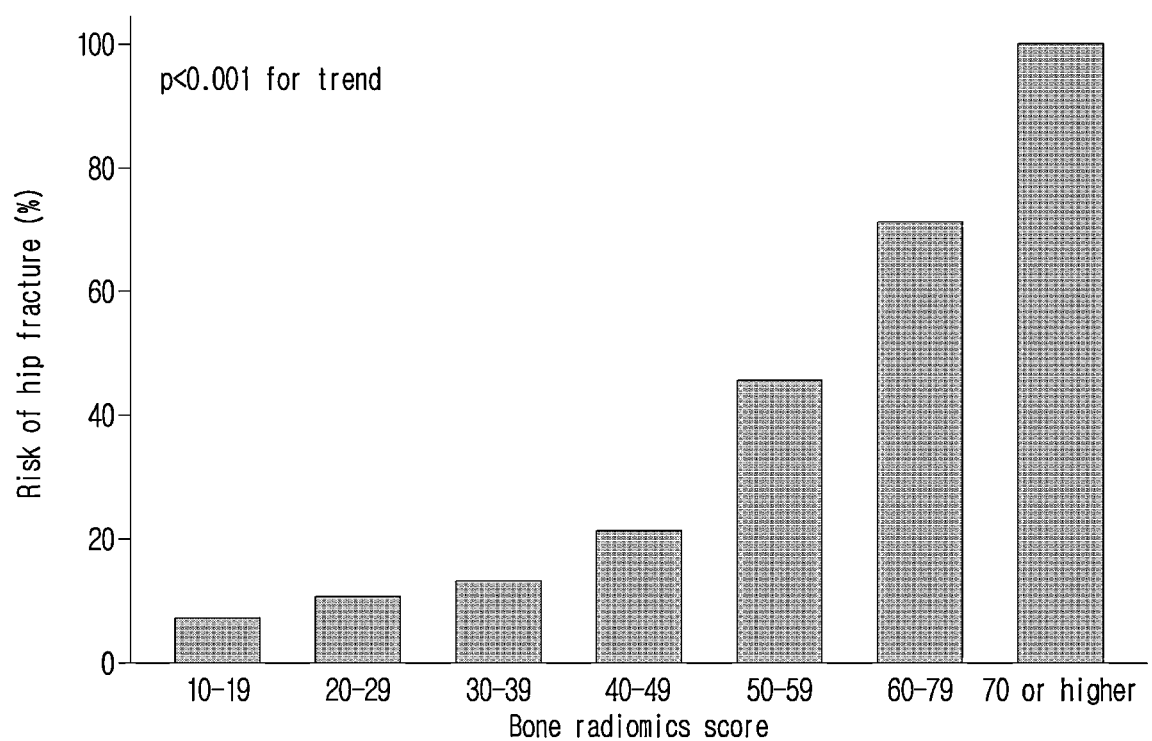
FIG. 8 is a diagram for describing a relation between a bone radiomics score model and fracture risk.

The risk of incident hip fracture during a follow-up period was increased in stepwise with bone radiomics score deciles. FIG. 8 is a diagram for describing a hip fracture prediction result using a bone radiomics score model.

The bone radiomics score model may be displayed in 10 units. Referring to FIG. 8, a vertical axis represents the risk of hip fracture, and a horizontal axis represents a bone radiomics score. Referring to FIG. 8, it can be seen that the higher the bone radiomics score, the higher an injury rate (fracture risk) of hip.

Figure 9A:
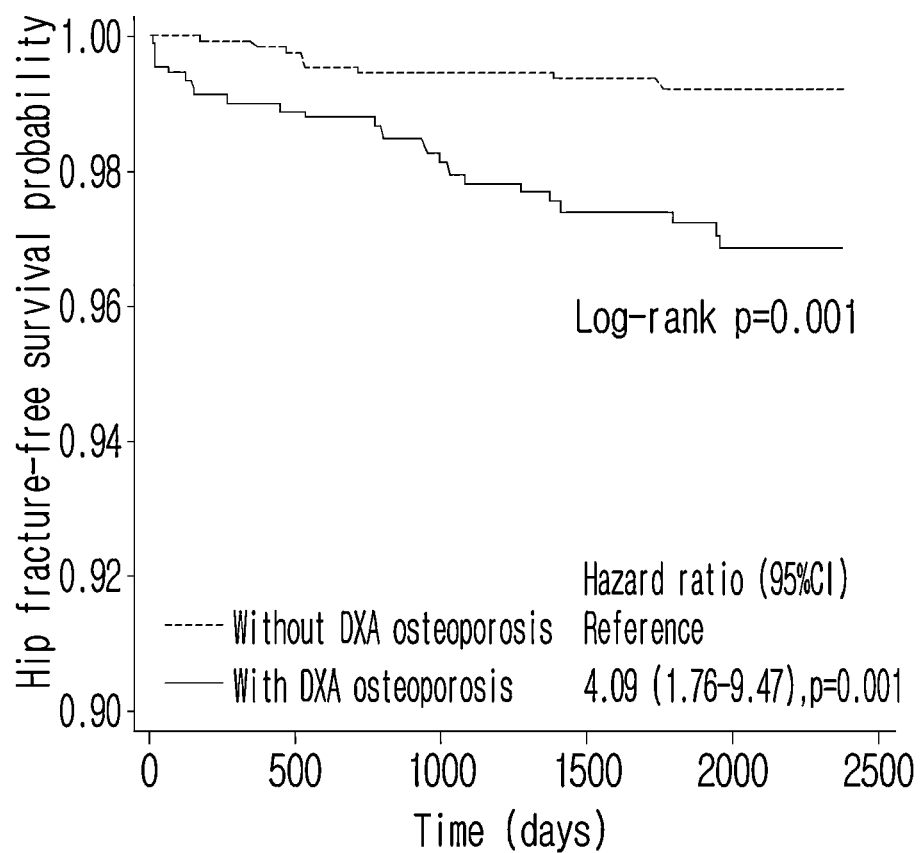
FIG. 9A illustrates a DXA-based osteoporosis chart.
Figure 9B:
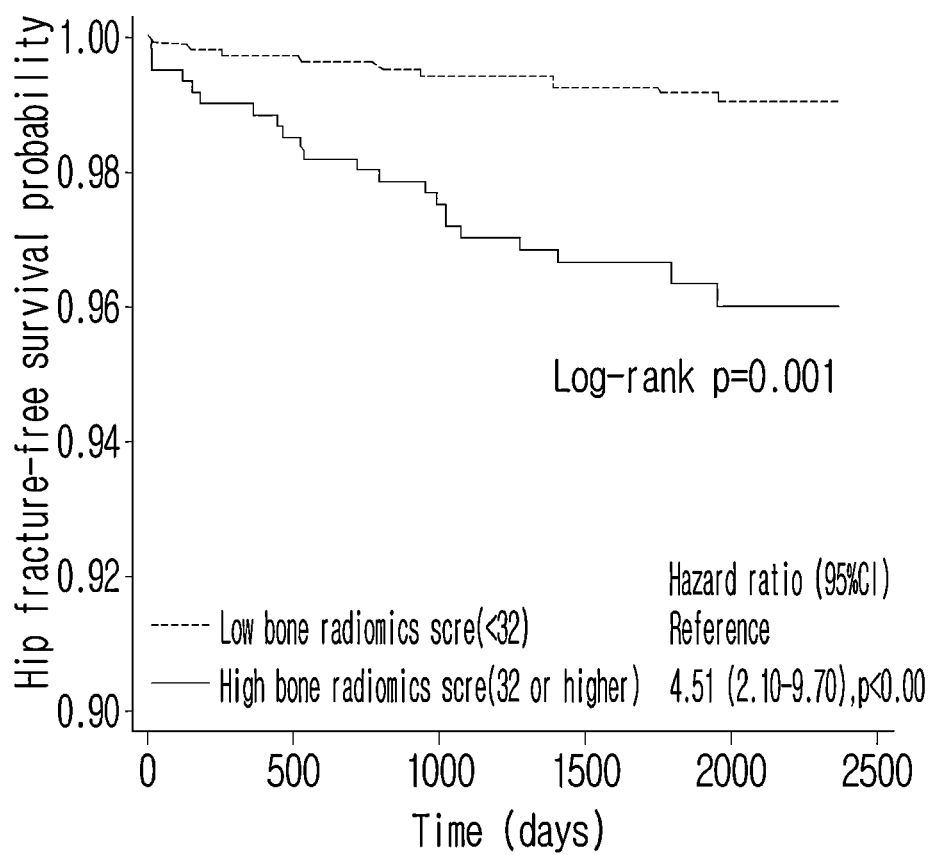
FIG. 9B illustrates a bone radiomics score.
Figure 9C:
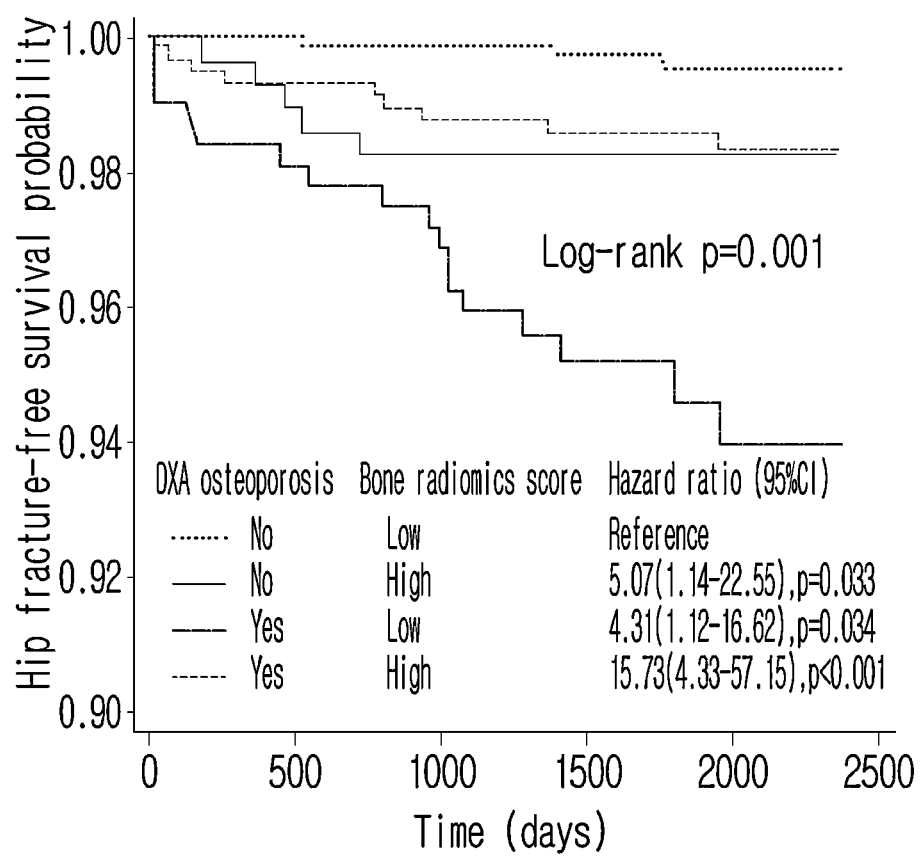
FIG. 9C illustrates a combination of DXA-based osteoporosis and bone radiomics score in the validation cohort.

FIGS. 9A to 9C shows a Kaplan-Meier survival chart for incident hip fracture.

FIG. 9A illustrates a DXA-based osteoporosis chart, FIG. 9B illustrates a bone radiomics score, and FIG. 9C illustrates a combination of DXA-based osteoporosis and bone radiomics score in the validation cohort. In FIGS. 9A to 9C, a vertical axis represents a hip fracture-free survival probability, and a horizontal axis represents a time based on days.

In FIGS. 9A to 9C, individuals with DXA osteoporosis or high bone radiomics score (32 or higher) had lower cumulative hip fracture-free survival probability than those without DXA osteoporosis (FIG. 9: DXA osteoporosis vs. without DXA osteoporosis: log-rank p=0.001, hazard ratio [HR] 4.09, 95% CI 1.76-9.47, p=0.001; high bone radiomics score vs. without bone radiomics score: log-rank p<0.001, HR 4.51, 95% CI 2.10-9.70, p<0.001). Compared to individuals without DXA osteoporosis and with low bone radiomics score, those without DXA osteoporosis but with high bone radiomics score had about 5-fold higher risk for hip fracture (HR 5.07 [95% CI 0.14-22.55], p=0.033). It was similar to the risk of subjects with DXA osteoporosis and low bone radiomics score (HR 4.31, 95% CI 1.12-16.62, p=0.034). Individuals with DXA osteoporosis and high radiomics bone score had the highest hip fracture risk (HR 15.73, 95% CI 4.33-57.15, p<0.001) among all groups (log-rank P<0.001), which was independent for a FRAX hip fracture probability (adjusted HR 8.25, 95% CI 2.41-28.23, p=0.001; see Table 5)

TABLE 5

| Incident hip fracture prediction | Univariate model | | Multivariate model | |
|---|---|---|---|---|
| | Not adjusted HR (95% CI) | P value | Adjusted HR (95% CI) | P value |
| DXA osteoporosis/ Bone Radiomics Score | | | | |
| No/Low | 1.00 (reference) | | 1.00 (reference) | |
| No / High | 5.07 (1.14-22.55) | 0.033 | 4.49 (1.03-19.50) | 0.045 |
| Yes / Low | 4.31 (1.12-16.62) | 0.034 | 2.52 (0.71-9.02) | 0.155 |
| Yes / High | 15.73 (4.33-57.15) | <0.001 | 8.25 (2.41-28.23) | 0.001 |
| FRAX hip fracture probability (> 3%) | 7.25 (2.14-24.50) | 0.001 | 3.68 (1.06-12.74) | 0.040 |

TABLE 6

| Incident hip fracture prediction | Univariate model | | Multivariate model 1 | | Multivariate model 2 | |
|---|---|---|---|---|---|---|
| | Not adjusted HR (95% CI) | P value | Adjusted HR (95% CI) | P value | Adjusted HR (95% CI) | P value |
| Age (whenever 5 years are increased) | 2.07 (1.29-3.32) | 0.003 | 1.36 (0.80-2.28) | 0.252 | 1.14 (0.64-2.04) | 0.655 |
| Fracture history (Yes or No)c | 5.81 (2.57-13.12) | <0.001 | 3.79 (1.58-9.04) | 0.003 | 3.15 (1.21-8.17) | 0.018 |
| Femoral neck T score (per 0.1 T score reduction) | 1.13 (1.07-1.20) | <0.001 | 1.09 (1.03-1.15) | 0.002 | 1.08 (1.01-1.15) | 0.020 |
| Bone radiomics score (per 1-point increase) | 1.07 (1.04-1.11) | <0.001 | — | — | 1.04 (1.00-1.09) | 0.043 |
| Harrel's C index (95% CI) | Bone radiomics score alone: 0.73 (0.63-0.82) | | Model 1: 0.80 (0.72-0.88) | | Model 2: 0.85 (0.78-0.92)* | |

Tabe 5 shows analyzing bone radiomics score values for independent hip fracture prediction of DXA osteoporosis and FRAX scores.

One-point increase in bone radiomics score was associated with 7% increased risk for hip fracture (HR 1.07, 95% CI 1.04-1.11, p<0.001), which remained robust after adjustment for covariates (adjusted HR 1.04, 95% CI 1.00-1.09, p=0.043; see Table 6). The bone radiomics score alone showed modest discrimination for hip fracture (Harrel's C index 0.73, 95% CI 0.63 to 0.83), which may be significantly improved when added to age, previous history of fragility fracture, and femoral neck T-score. In Table 6, Multivariate Model 1 represents result values considered with age, fracture history, and femoral neck T-score as fracture predictors. That is, Multivariate Model 1 represents fracture risk prediction result values when the bone radiomics score is not applied, and Multivariate Model 2 represents result values when the bone radiomics score is applied to Multivariate Model 1. Accordingly, when the bone radiomics score is added to Multivariate Model 1, it is shown that a C index (discrimination, good model closer to 1.00) for the hip fracture risk prediction is improved to 0.80 to 0.85 (p=0.040).

Figure 10:
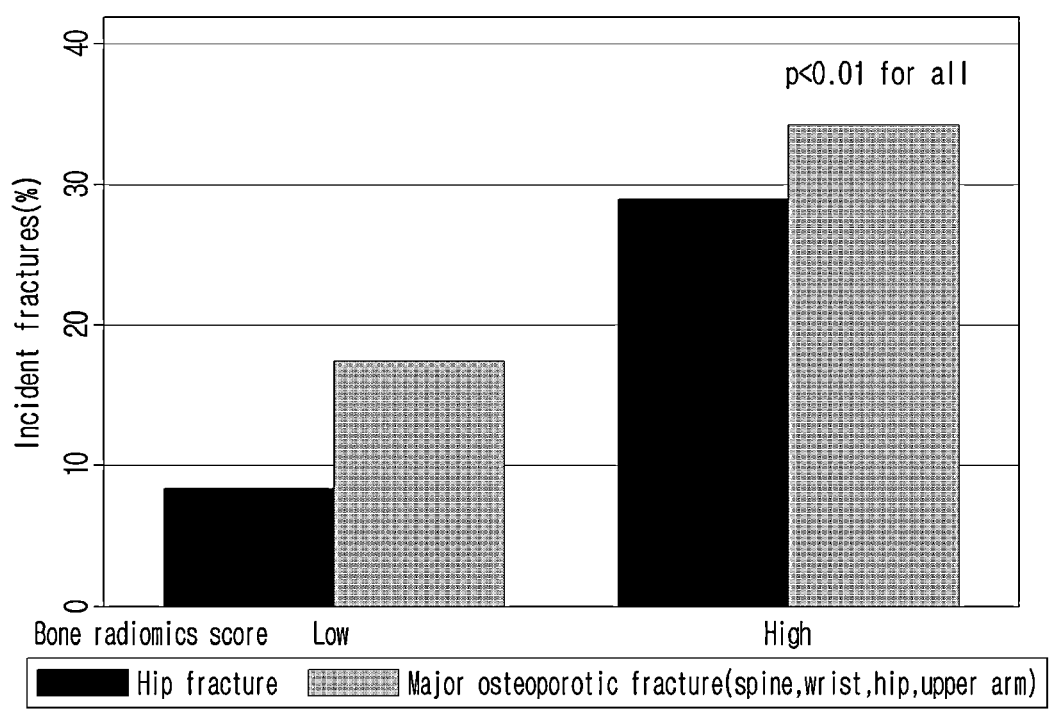
FIG. 10 illustrates a difference in major osteoporotic fracture risk between a group with a high bone radiomics score and a group with a low bone radiomics score.

FIG. 10 illustrates comparing major osteoporotic fracture risk (spine, wrist, upper arm, and femoral fracture) including femoral fracture between a group with a high bone radiomics score and a group with a low bone radiomics score, and the following Table 7 is a table of comparing differences between a univariate model and a multivariate model associated with the occurrence of osteoporotic fracture.

As illustrated in FIG. 10, in the group with the high bone radiomics score, the major osteoporotic fracture risk such as spine, wrist, upper arm, and femoral fracture was 34%, which was significantly higher than 17% in the group with the low bone radiomics score.

Further, as illustrated in Table 7, it can be confirmed that as the bone radiomics score increases by 1 point, the risk of osteoporotic fracture (spine, wrist, upper arm, femoral fracture) increases by 4%. The increase in the bone radiomics score was an independent predictor of age, osteoporosis, and existing fracture (adjusted odds ratio 1.03, 95% CI 1.01-1.06, p=0.019).

TABLE 7

| | Univariate | | | Multivariate | | |
|---|---|---|---|---|---|---|
| | Odds ratio | 95% CI | P value | Odds ratio | 95% CI | P value |
| Bone radiomics score (1 point is increased) | 1.04 | 1.02-1.07 | <0.001 | 1.03 | 1.01-1.06 | 0.019 |
| Age | 1.10 | 1.06-1.13 | <0.001 | 1.11 | 1.02-1.20 | |
| Osteoporosis | 2.21 | 1.66-2.94 | <0.001 | 1.66 | 0.78-3.51 | 0.182 |
| Fracture history | 2.59 | 1.96-3.43 | <0.001 | 3.85 | 1.89-7.85 | <0.001 |

TABLE 2

| Based methods | Parameter | Formula | Description |
|---|---|---|---|
| | Grey Level Co-occurrence Matrix (GLCM): A Gray Level Co-occurrence Matrix (GLCM) of size Ng × Ng describes the second-order joint probability function of an image region constrained by th emask and is defined as P(i,j|δ,θ). The (i,j)th element of this matrix represents the number of times the combination of levels i and j occur in two pixels in the image, that are separated by a distance of δ pixels along angle θ. | | |
| GLCM Features | Autocorrelation | $$\text{autocorrelation} = \sum_{i=1}^{N_g}\sum_{j=1}^{N_g} p(i,j)ij$$ | Autocorrelation is a measure of the magnitude of the fineness and coarseness of texture. |
| | Joint Average | $$\text{joint average} = \mu_x = \sum_{i=1}^{N_g}\sum_{j=1}^{N_g} p(i,j)i$$ | The mean gray level intensity of the I distribution. |
| | Cluster Prominence | $$\text{cluster prominence} = \sum_{i=1}^{N_g}\sum_{j=1}^{N_g}(i+j-\mu_x-\mu_y)^4 p(i,j)$$ | Cluster Prominence is a measure of the skewness and asymmetry of the GLCM. A higher values implies more asymmetry about the mean while a lower value indicates a peak near the mean value and less variation about the mean. |
| | Cluster Shade | $$\text{cluster shade} = \sum_{i=1}^{N_g}\sum_{j=1}^{N_g}(i+j-\mu_x-\mu_y)^3 p(i,j)$$ | Cluster Shade is a measure of the skewness and uniformity of the GLCM. A higher cluster shade implies greater asymmetry about the mean. |
| | Cluster Tendency | $$\text{cluster tendency} = \sum_{i=1}^{N_g}\sum_{j=1}^{N_g}(i+j-\mu_x-\mu_y)^2 p(i,j)$$ | Cluster Tendency is a measure of groupings of voxels with similar gray-level values. |
| | Contrast | $$\text{cluster tendency} = \sum_{i=1}^{N_g}\sum_{j=1}^{N_g}(i+j)^2 p(i,j)$$ | Contrast is a measure of the local intensity variation, favoring values away from the diagonal. A larger value correlates with a greater disparity in intensity values among neighboring voxels. |
| | Correlation | $$\text{correlation} = \frac{\sum_{i=1}^{N_g}\sum_{j=1}^{N_g} p(i,j)ij - \mu_x\mu_y}{\sigma_x(i)\sigma_y(j)}$$ | Correlation is a value between 0 (uncorrelated) and 1 (perfectly correlated) showing the linear dependency of gray level values to their respective voxels in the GLCM. |
| | Difference Average | $$\text{difference average} = \sum_{k=0}^{N_g-1} k p_{x-y}(k)$$ | Difference Average measures the relationship between occurrences of pairs with similar intensity values and occurrences of pairs with differing intensity values. |
| | Difference Entropy | $$\text{difference entropy} = \sum_{k=0}^{N_g-1} p_{x-y}(k)\log_2(p_{x-y}(k)+\epsilon)$$ | Difference Entropy is a measure of the randomness/variability in neighborhood intensity value differences |

TABLE 2-continued

| Based methods | Parameter | Formula | Description |
|---|---|---|---|
| | Difference Variance | $$\text{difference variance} = \sum_{k=0}^{N_g-1} (k - DA)^2 p_{x-y}(k)$$ | Difference Variance is a measure of heterogeneity that places higher weights on differing intensity level pairs that deviate more from the mean. |
| | Joint Energy | $$\text{joint entropy} = \sum_{i=1}^{N_g} \sum_{j=1}^{N_g} (p(i,j))^2$$ | Energy is a measure of homogeneous patterns in the image. A greater Energy implies that there are more instances of intensity value pairs in the image that neighbor each other at higher frequencies. |
| | Joint Entropy | $$\text{joint entropy} = -\sum_{i=1}^{N_g} \sum_{j=1}^{N_g} (p(i,j) \log_2(p(i,j) + \epsilon)$$ | Joint entropy is a measure of the randomness/variability in neighborhood intensity values. |
| | Informational Measure of Correlation (IMC) 1 | $$IMC1 = \frac{HXY - HXY1}{\max\{HX, HY\}}$$ | This class of features characterizes the textures of an image/object by creating a new matrix GLCM based on counting how often pairs of pixels with specific gray-level values and in a specified spatial relationship (distance and direction) occur in the image/object and then computing statistics from GLCM · IMC1 assesses the correlation between each and every probability distribution (quantifying the complexity of the texture). It represents the information of a single distribution. |
| | Informational Measure of Correlation (IMC) 2 | $$IMC2 = \sqrt{1 - e^{-2(HXY2-HXY)}}$$ | IMC2 also assesses the correlation between each and every probability distribution (quantifying the complexity of the texture). It represents the information of two of the distributions. |
| | Inverse Difference Moment (IDM) | $$IDM = \sum_{k=0}^{N_g-1} \frac{p_{x-y}(k)}{1 + k^2}$$ | IDM is a measure of the local homogeneity of an image. IDM weights are the inverse of the Contrast weights. |
| | Maximal Correlation Coefficient (MCC) | $$MCC = \sqrt{\text{second largest eigenvalue of } Q}$$ $$Q(i,j) = \sum_{k=0}^{N_g} \frac{p(i,k)p(j,k)}{p_x(i)p_y(k)}$$ | The Maximal Correlation Coefficient is a measure of complexity of the texture and $0 \leq MCC \leq 1$. |
| | Inverse Difference Moment Normalized (IDMN) | $$IDMN = \sum_{k=0}^{N_g-1} \frac{p_{x-y}(k)}{1 + \left(\frac{k^2}{N_g^2}\right)}$$ | IDMN (inverse difference moment normalized) is a measure of the local homogeneity of an image. IDMN weights are the inverse of the Contrast weights. |
| | Inverse Difference (ID) | $$ID = \sum_{k=0}^{N_g-1} \frac{p_{x-y}(k)}{1 + k}$$ | ID is another measure of the local homogeneity of an image. With more uniform gray levels, the denominator will remain low, resulting in a higher overall value. |
| | Inverse Difference Normalized (IDN) | $$IDN = \sum_{k=0}^{N_g-1} \frac{p_{x-y}(k)}{1 + \left(\frac{k}{N_g}\right)}$$ | IDN is another measure of the local homogeneity of an image |
| | Inverse Variance | $$\text{inverse variance} = \sum_{k=0}^{N_g-1} \frac{p_{x-y}(k)}{k^2}$$ | Inverse of the variance calculated is taken |
| | Maximum Probability | $$\text{maximum probability} = \max(p(i,j))$$ | Maximum Probability is occurrences of the most predominant pair of neighboring intensity values. |

TABLE 2-continued

| Based methods | Parameter | Formula | Description |
|---|---|---|---|
| | Sum Average | $$\text{sum average} = \sum_{k=2}^{2N_g} p_{x-y}(k)k$$ | Sum Average measures the relationship between occurrences of pairs with lower intensity values and occurrences of pairs with higher intensity values. |
| | Sum Entropy | $$\text{sum entrophy} = \sum_{k=2}^{2N_g} p_{x-y}(k)\log_2(p_{x-y}(k) + \epsilon)$$ | Sum Entropy is a sum of neighborhood intensity value differences. |
| | Sum of Squares | $$\text{sum squares} = \sum_{i=1}^{N_g}\sum_{j=1}^{N_g}(i-\mu_x)^2 p(i,j)$$ | Sum of Squares or Variance is a measure in the distribution of neighboring intensity level pairs about the mean intensity level in the GLCM. |

Gray Level Size Zone Matrix (GLSZM): A Gray Level Size Zone (GLSZM) quantifies gray level zones in an image. A gray level zone is defined as a the number of connected voxels that share the same gray level intensity. A voxel is considered connected if the distance is 1 according to the infinity norm (26-connected region in a 3D, 8-connected region in 2D). In a gray level size zone matrix P(i,j) the (i,j)th element equals the number of zones with gray level i and size j appear in image.

| Based methods | Parameter | Formula | Description |
|---|---|---|---|
| GLSZM features | Small Area Emphasis (SAE) | $$SAE = \frac{\sum_{i=1}^{N_g}\sum_{j=1}^{N_s}\frac{P(i,j)}{j^2}}{N_z}$$ | SAE is a measure of the distribution of small size zones, with a greater value indicative of more smaller size zones and more fine textures. |
| | Large Area Emphasis (LAE) | $$LAE = \frac{\sum_{i=1}^{N_g}\sum_{j=1}^{N_s}P(i,j)j^2}{N_z}$$ | LAE is a measure of the distribution of large area size zones, with a greater value indicative of more larger size zones and more coarse textures. |
| | Gray Level Non-Uniformity (GLN) | $$GLN = \frac{\sum_{i=1}^{N_g}\left(\sum_{j=1}^{N_s}P(i,j)\right)^2}{N_z}$$ | GLN measures the variability of gray-level intensity values in the image, with a lower value indicating more homogeneity in intensity values. |
| | Gray Level Non-Uniformity Normalized (GLNN) | $$GLNN = \frac{\sum_{i=1}^{N_g}\left(\sum_{j=1}^{N_s}P(i,j)\right)^2}{N_z^2}$$ | GLNN measures the variability of gray-level intensity values in the image, with a lower value indicating a greater similarity in intensity values. This is the normalized version of the GLN formula. |
| | Size-Zone Non-Uniformity (SZN) | $$SZN = \frac{\sum_{j=1}^{N_s}\left(\sum_{i=1}^{N_g}P(i,j)\right)^2}{N_z}$$ | SZN measures the variability of size zone volumes in the image, with a lower value indicating more homogeneity in size zone volumes. |
| | Size-Zone Non-Uniformity Normalized (SZNN) | $$SZNN = \frac{\sum_{j=1}^{N_s}\left(\sum_{i=1}^{N_g}P(i,j)\right)^2}{N_z^2}$$ | SZNN measures the variability of size zone volumes throughout the image, with with a lower value indicating more homogeneity among zone size volumes in the image. This is the normalized version of the SZN formula. |
| | Zone Percentage (ZP) | $$ZP = \frac{N_z}{N_p}$$ | ZP measures the coarseness of the texture by taking the ratio of number of zones and number of voxels in the ROI. |
| | Gray Level Variance (GLV) | $$GLN = \sum_{i=1}^{N_g}\sum_{j=1}^{N_g}p(i,j)(j-\mu)^2$$ | GLV measures the variance in gray level intensities for the zones. |
| | Zone Variance (ZV) | $$ZV = \sum_{i=1}^{N_g}\sum_{j=1}^{N_s}p(i,j)(j-\mu)^2$$ | ZV measures the variance in zone size volumes for the zones. |
| | Zone Entropy (ZE) | $$ZE = \sum_{i=1}^{N_g}\sum_{j=1}^{N_s}p(i,j)\log_2(p(i,j) + \epsilon)$$ | ZE measures the uncertainty/randomness in the distribution of zone sizes and gray levels. A higher value indicates more heterogeneneity in the texture patterns. |
| | Low Gray Level Zone Emphasis (LGLZE) | $$LGLZE = \frac{\sum_{i=1}^{N_g}\sum_{j=1}^{N_s}\frac{P(i,j)}{i^2}}{N_z}$$ | LGLZE measures the distribution of lower gray-level size zones, with a higher value indicating a greater proportion of lower gray-level values and size zones in the image. |

TABLE 2-continued

| Based methods | Parameter | Formula | Description |
|---|---|---|---|
| | High Gray Level Zone Emphasis (HGLZE) | $HGLZE = \dfrac{\sum_{i=1}^{N_g}\sum_{j=1}^{N_s} P(i,j)i^2}{N_z}$ | HGLZE measures the distribution of the higher gray-level values, with a higher value indicating a greater proportion of higher gray-level values and size zones in the image. |
| | Small Area Low Gray Level Emphasis (SALGLE) | $SALGLE = \dfrac{\sum_{i=1}^{N_g}\sum_{j=1}^{N_s} \dfrac{P(i,j)}{i^2 j^2}}{N_z}$ | SALGLE measures the proportion in the image of the joint distribution of smaller size zones with lower gray-leval values. |
| | Small Area High Gray Level Emphasis (SAHGLE) | $SAHGLE = \dfrac{\sum_{i=1}^{N_g}\sum_{j=1}^{N_s} \dfrac{P(i,j)i^2}{j^2}}{N_z}$ | SAHGLE measures the proportion in the image of the joint distribution of smaller size zones with higher gray-level values. |
| | Large Area Low Gray Level Emphasis (LALGLE) | $LALGLE = \dfrac{\sum_{i=1}^{N_g}\sum_{j=1}^{N_s} \dfrac{P(i,j)j^2}{i^2}}{N_z}$ | LALGLE measures the proportion in the image of the joint distribution of larger size zones with lower gray-level values. |
| | Large Area High Gray Level Emphasis (LAHGLE) | $LAHGLE = \dfrac{\sum_{i=1}^{N_g}\sum_{j=1}^{N_s} P(i,j)i^2 j^2}{N_z}$ | LAHGLE measures the proportion in the image of the joint distribution of larger size zones with higher gray-level values. |

Gray Level Run Length Matrix (GLRLM): A Gray Level Run Length Matrix (GLRLM) quantifies gray level runs, which are defined as the length in number of pixels, of consecutive pixels that have the same gray level value. In a gray level run length matrix $P(i,j|\theta)$, the (i,j)th element describes the number of runs with gray level i and length j occur in the image (ROI) along angle $\theta$.

| Based methods | Parameter | Formula | Description |
|---|---|---|---|
| GLRLM features | Short Run Emphasis (SRE) | $SRE = \dfrac{\sum_{i=1}^{N_g}\sum_{j=1}^{N_r} \dfrac{P(i,j|\theta)}{j^2}}{N_r(\theta)}$ | SRE is a measure of the distribution of short run lengths, with a greater value indicative of shorter run lengths and more fine textural textures. |
| | Long Run Emphasis (LRE) | $LRE = \dfrac{\sum_{i=1}^{N_g}\sum_{j=1}^{N_r} P(i,j|\theta)j^2}{N_r(\theta)}$ | LRE is a measure of the distribution of long run lengths, with a greater value indicative of longer run lengths and more coarse structural textures. |
| | Gray Level Non-Uniformity (GLN) | $GLN = \dfrac{\sum_{i=1}^{N_g}\left(\sum_{j=1}^{N_r} P(i,j|\theta)\right)}{N_r(\theta)}$ | GLN measures the similarity of gray-level intensity values in the image, where a lower GLN value correlates with a greater similarity in intensity values. |
| | Gray Level Non-Uniformity Normalized (GLNN) | $GLNN = \dfrac{\sum_{i=1}^{N_g}\left(\sum_{j=1}^{N_r} P(i,j|\theta)\right)^2}{N_r(\theta)^2}$ | GLNN measures the similarity of gray-level intensity values in the image, where a lower GLNN value correlates with a greater similarity in intensity values. This is the normalized version of the GLN formula. |
| | Run Length Non-Uniformity (RLN) | $RLN = \dfrac{\sum_{j=1}^{N_r}\left(\sum_{i=1}^{N_g} P(i,j|\theta)\right)^2}{N_r(\theta)}$ | RLN measures the similarity of run lengths throughout the image, with a lower value indicating more homogeneity among run lengths in the image. |
| | Run Length Non-Uniformity Normalized (RLNN) | $RLNN = \dfrac{\sum_{j=1}^{N_r}\left(\sum_{i=1}^{N_g} P(i,j|\theta)\right)^2}{N_r(\theta)^2}$ | RLNN measures the similarity of run lengths throughout the image, with a lower value indicating more homogeneity among run lengths in the image. This is the normalized version of the RLN formula. |
| | Run Percentage (RP) | $RLNN = \dfrac{N_r(\theta)}{N_p}$ | RP measures the coarseness of the texture by taking the ratio of number of runs and number of voxels in the ROI. |
| | Gray Level Variance (GLV) | $GLV = \sum_{i=1}^{N_g}\sum_{j=1}^{N_r} p(i,j|\theta)(i-\mu)^2$ | GLV measures the variance in gray level intensity for the runs. |

TABLE 2-continued

| Based methods | Parameter | Formula | Description |
|---|---|---|---|
| | Run Variance (RV) | $RV = \sum_{i=1}^{N_g}\sum_{j=1}^{N_r} p(i,j|\theta)(j-\mu)^2$ | RV is a measure of the variance in runs for the run lengths. |
| | Run Entropy (RE) | $RE = -\sum_{i=1}^{N_g}\sum_{j=1}^{N_r} p(i,j|\theta)\log_2(p(i,j|\theta)+\epsilon)$ | RE measures the uncertainty/randomness in the distribution of run lengths and gray levels. A higher value indicates more heterogeneity in the texture patterns. |
| | Low Gray Level Run Emphasis (LGLRE) | $LGLRE = \dfrac{\sum_{i=1}^{N_g}\sum_{j=1}^{N_r} \dfrac{P(i,j|\theta)}{i^2}}{N_r(\theta)}$ | LGLRE measures the distribution of low gray-level values, with a higher value indicating a greater concentration of low gray-level values in the image. |
| | High Gray Level Run Emphasis (HGLRE) | $HGLRE = \dfrac{\sum_{i=1}^{N_g}\sum_{j=1}^{N_r} \dfrac{P(i,j|\theta)i^2}{i^2 j^2}}{N_r(\theta)}$ | HGLRE measures the distribution of the higher gray-level values, with a higher value indicating a greater concentration of high gray-level values in the image. |
| | Short Run Low Gray Level Emphasis (SRLGLE) | $SRLGLE = \dfrac{\sum_{i=1}^{N_g}\sum_{j=1}^{N_r} \dfrac{P(i,j|\theta)}{i^2 j^2}}{N_r(\theta)}$ | SRLGLE measures the joint distribution of shorter run lengths with lower gray-level values. |
| | Short Run High Gray Level Emphasis | $SBHGLE = \dfrac{\sum_{i=1}^{N_g}\sum_{j=1}^{N_r} \dfrac{P(i,j|\theta)i^2}{j^2}}{N_r(\theta)}$ | SRHGLE measures the joint distribution of shorter run lengths with higher gray-level values. |
| | Long Run Low Gray Level Emphasis (LRLGLE) | $LRLGLRE = \dfrac{\sum_{i=1}^{N_g}\sum_{j=1}^{N_r} \dfrac{P(i,j|\theta)j^2}{i^2}}{N_r(\theta)}$ | LRLGLRE measures the joint distribution of long run lengths with lower gray-level values. |
| | Long Run High Gray Level Emphasis (LRHGLE) | $LRHGLRE = \dfrac{\sum_{i=1}^{N_g}\sum_{j=1}^{N_r} P(i,j|\theta)i^2 j^2}{N_r(\theta)}$ | LRHGLRE measures the joint distribution of long run lengths with higher gray-level values. |

Gray Level Dependence Matrix (GLDM): A Gray Level Dependence Matrix (GLDM) quantifies gray level dependencies in an image. A gray level dependency is defined as a the number of connected voxels within distance δ that are dependent on the center voxel. A neighbouring voxel with gray level j is considered dependent on center voxel with gray level i if |i-j| ≤ α. In a gray level dependence matrix P(i,j) the (i,j)th element describes the number of times a voxel with gray level i with j dependent voxels in its neighbourhood appears in image.

| Based methods | Parameter | Formula | Description |
|---|---|---|---|
| GLDM Large | Small Dependence Emphasis (SDE) | $SDE = \dfrac{\sum_{i=1}^{N_g}\sum_{j=1}^{N_r} \dfrac{P(i,j)}{i^2}}{N_z}$ | A measure of the distribution of small dependencies, with a greater value indicative of smaller dependence and less homogeneous textures. |
| | Large Dependence Emphasis (LDE) | $LDE = \dfrac{\sum_{i=1}^{N_g}\sum_{j=1}^{N_r} \dfrac{P(i,j)j^2}{i^2}}{N_z}$ | A measure of the distribution of large dependencies, with a greater value indicative of larger dependence and more homogeneous textures. |
| | Gray Level Non-Uniformity (GLN) | $GLN = \dfrac{\sum_{i=1}^{N_g}\left(\sum_{j=1}^{N_d} P(i,j)\right)^2}{N_z}$ | Measures the similarity of gray-level intensity values in the image, where a lower GLN value correlates with a greater similarity in intensity values. |
| | Dependence Non-Uniformity (DN) | $DN = \dfrac{\sum_{j=1}^{N_d}\left(\sum_{i=1}^{N_g} P(i,j)\right)^2}{N_z}$ | Measures the similarity of dependence throughout the image, with a lower value indicating more homogeneity among dependencies in the image. |
| | Dependence Non-Uniformity Normalized (DNN) | $DNN = \dfrac{\sum_{j=1}^{N_d}\left(\sum_{i=1}^{N_g} P(i,j)\right)^2}{N_z^2}$ | Measures the similarity of dependence throughout the image, with a lower value indicating more homogeneity among dependencies in the image. This is the normalized version of the DLN formula. |

TABLE 2-continued

| Based methods | Parameter | Formula | Description |
|---|---|---|---|
| | Gray Level Variance (GLV) | $GLV = \sum_{i=1}^{N_g} \sum_{j=1}^{N_d} p(i,j)(i-\mu)^2,$ where $\mu = \sum_{i=1}^{N_g} \sum_{j=1}^{N_d} ip(i,j)$ | Measures the variance in grey level in the image. |
| | Dependence Variance (DV) | $DV = \sum_{i=1}^{N_g} \sum_{j=1}^{N_d} p(i,j)(j-\mu)^2,$ where $\mu = \sum_{i=1}^{N_g} \sum_{j=1}^{N_d} jp(i,j)$ | Measures the variance in dependence size in the image. |
| | Dependence Entropy (DE) | $\text{Dependence Entrophy} = -\sum_{i=1}^{N_g} \sum_{j=1}^{N_d} p(i,j) \log_2(p(i,j)+\epsilon)$ | The randomness of GLDM. Higher Dependence Entropy implies more complex texture |
| | Low Gray Level Emphasis (LGLE) | $LGLE = \dfrac{\sum_{i=1}^{N_g} \sum_{j=1}^{N_d} \frac{P(i,j)}{i^2}}{N_z}$ | Measures the distribution of low gray-level values, with a higher value indicating a greater concentration of low gray-level values in the image. |
| | High Gray Level Emphasis (HGLE) | $HGLE = \dfrac{\sum_{i=1}^{N_g} \sum_{j=1}^{N_d} P(i,j)i^2}{N_z}$ | Measures the distribution of the higher gray-level values, with a higher value indicating a greater concentration of high gray-level values in the image. |
| | Small Dependence Low Gray Level Emphasis (SDLGLE) | $SDLGLE = \dfrac{\sum_{i=1}^{N_g} \sum_{j=1}^{N_d} \frac{P(i,j)}{i^2 j^2}}{N_z}$ | Measures the joint distribution of small dependence with lower gray-level values. |
| | Small Dependence High Gray Level Emphasis (SDHGLE) | $SDHGLE = \dfrac{\sum_{i=1}^{N_g} \sum_{j=1}^{N_d} \frac{P(i,j)i^2}{j^2}}{N_z}$ | Measures the joint distribution of small dependence with higher gray-level values. |
| | Large Dependence Low Gray Level Emphasis (LDLGLE) | $LDLGLE = \dfrac{\sum_{i=1}^{N_g} \sum_{j=1}^{N_d} \frac{P(i,j)j^2}{i^2}}{N_z}$ | Measures the joint distribution of large dependence with lower gray-level values. |
| | Large Dependence High Gray Level Emphasis (LDHGLE) | $LDHGLE = \dfrac{\sum_{i=1}^{N_g} \sum_{j=1}^{N_d} P(i,j)i^2 j^2}{N_z}$ | Measures the joint distribution of large dependence with higher gray-level values. |

Neighbouring Gray Tone Difference Matrix (NGTDM): A Neighbouring Gray Tone Difference Matrix quantifies the difference between a gray value and the average gray value of its neighbours within distance δ.

| NGTDM features | Coarseness | $\text{Coarseness} = \dfrac{1}{\sum_{i=1}^{N_g} p_i s_i}$ | Coarseness is a measure of average difference between the center voxel and its neighbourhood and is an indication of the spatial rate of change. A higher value indicates a lower spatial change rate and a locally more uniform texture. |

TABLE 2-continued

| Based methods | Parameter | Formula | Description |
|---|---|---|---|
| | Contrast | $\text{Contrast} = \left( \dfrac{1}{N_{g,p}(N_{g,p}-1)} \sum_{i=1}^{N_g} \sum_{j=1}^{N_g} p_i p_j (i-j)^2 \right)\left( \dfrac{1}{N_{v,p}} \sum_{i=1}^{N_g} s_i \right)$, where $p_i \neq 0, p_j \neq 0$ | Contrast is a measure of the spatial intensity change, but is also dependent on the overall gray level dynamic range. Contrast is high when both the dynamic range and the spatial change rate are high, i.e. an image with a large range of gray levels, with large changes between voxels and their neighbourhood. |
| | Busyness | $\text{Busyness} = \dfrac{\sum_{i=1}^{N_g} p_i s_i}{\sum_{i=1}^{N_g}\sum_{j=1}^{N_g}|ip_i - jp_j|}$, where $p_i \neq 0, p_j \neq 0$ | A measure of the change from a pixel to its neighbour. A high value for busyness indicates a 'busy' image, with rapid changes of intensity between pixels and its neighbourhood. |
| | Complexity | $\text{Complexity} = \dfrac{1}{N_{v,p}} \sum_{i=1}^{N_g}\sum_{j=1}^{N_g} |i-j|\dfrac{p_i s_i + p_j s_j}{p_i + p_j}$, where $p_i \neq 0, p_j \neq 0$ | An image is considered complex when there are many primitive components in the image, i.e. the image is non-uniform and there are many rapid changes in gray level intensity. |
| | Strength | $\text{Strength} = \dfrac{\sum_{i=1}^{N_g}\sum_{j=1}^{N_g}(p_i + p_j)(i-j)^2}{\sum_{i=1}^{N_g} s_i}$, where $p_i \neq 0, p_j \neq 0$ | Strength is a measure of the primitives in an image. Its value is high when the primitives are easily defined and visible, i.e. an image with slow change in intensity but more large coarse differences in gray level intensities. |

The embodiments of the present invention described above may be embodied in other specific forms without departing from the spirit and essential characteristics of the present invention. Accordingly, the aforementioned detailed description should not be construed as restrictive in all terms and should be exemplarily considered. The scope of the present invention should be determined by rational construing of the appended claims and all modifications within an equivalent scope of the present invention are included in the scope of the present invention. Further, the claims that are not expressly cited in the claims are combined to form an exemplary embodiment or be included in a new claim by an amendment after the application.

The invention claimed is:

1. A method of predicting fracture risk comprising the steps of:
providing a development set;
processing bone images for a plurality of subjects included in the development set;
extracting texture features from the processed bone images;
selecting optimal texture features required to predict the fracture risk from the extracted texture features;
performing machine learning operations for predicting fracture risk based on the selected optimal texture features using a training set of the development set; and
defining a bone radiomics score model to predict the fracture risk based on the results of the machine learning operations.

2. The method of predicting the fracture risk of claim 1, wherein the machine learning is performed using one of a random forest model, an elastic net model, a gradient boosting decision tree model, and a support vector machine model.

3. The method of predicting the fracture risk of claim 2, wherein in the step of performing the machine learning;
the machine learning is performed by applying the optimal texture features to the random forest model, the elastic net model, the gradient boosting decision tree model, and the support vector machine model, respectively, and
one machine learning model is selected by evaluation result for each machine learning in the validation set.

4. The method of predicting the fracture risk of claim 1, wherein the bone images are a dual energy X-ray absorptiometry (DXA) hip images, four regions of interest corresponding to femoral neck, trochanter, intertochanter, and total hip are configured from the DXA hip images, and wherein in the step of processing the bone images, a preprocessing process for extracting texture features is performed with respect to the four regions of interest.

5. The method of predicting the fracture risk of claim 4, wherein the preprocessing process is performed by a process of masking the regions of interest in different colors for each region along generated guidance lines, removing the guidance lines, and then improving substrate patterns through contrast-limited adaptive histogram equalization and median filtering.

6. The method of predicting the fracture risk of claim 1, wherein the development set is provided as a development set in which a case group and a control group are matched at 1:A from a case group data base and a control group data base and;
a final development set is provided by removing unusable bone images from the matched development set.

7. The method of predicting the fracture risk of claim 1, wherein the optimal texture features include GLRLM (Gray Level Run Length Matrix) Run Entropy, GLRLM GLNN (Gray Level Non-uniformity Normalized), GLCM (Grey Level Co-occurrence Matrix) IMC1 (Information Measure of Correlation 1), GLCM IDMN (Inverse Difference Moment Normalized), GLCM Cluster Prominence, GLSZM SZN(Size-Zone Non-Uniformity), GLSZM (Gray Level Size Zone Matrix) SAHGLE (Small Area High Gray Level Emphasis), GLSZM (Gray Level Size Zone Matrix) GLN (Gray Level Non-Uniformity), GLSZM GLV (Gray Level Variance), and GLDM (Gray Level Dependence Matrix) DNN (Dependence Non-Uniformity Normalized).

8. The method of predicting the fracture risk of claim 1, wherein the bone image is a dual energy X-ray absorptiometry (DXA) image, and
   a step of predicting the DXA image to be tested as a high-risk group when the bone radiomics score is more than a predetermined threshold is further performed, as a step of predicting whether there is fracture risk or the degree of fracture risk using the bone radiomics score model.

9. A non-transitory computer reading medium storing computer program codes for predicting fracture risk, wherein when the computer program codes are executed by a computer, the computer is configured to perform the steps of:
   providing a development set;
   processing bone images for a plurality of subjects included in the development set;
   extracting texture features from the processed bone images;
   selecting optimal texture features required to predict the fracture risk from the extracted texture features;
   performing machine learning operations for predicting fracture risk based on the selected optimal texture features using a training set of the development set; and
   defining a bone radiomics score model to predict the fracture risk based on the results of the machine learning operations.

10. The computer reading medium of claim 9, wherein the machine learning is performed using one of a random forest model, an elastic net model, a gradient boosting decision tree model, and a support vector machine model.

11. The computer reading medium of claim 10, wherein in the step of performing the machine learning;
   the machine learning is performed by applying the optimal texture features to the random forest model, the elastic net model, the gradient boosting decision tree model, and the support vector machine model, respectively, and
   one machine learning model is selected by evaluation result for each machine learning in the validation set.

12. The computer reading medium of claim 9, wherein the bone images are a dual energy X-ray absorptiometry (DXA) hip images, four regions of interest corresponding to femoral neck, trochanter, intertochanter, and total hip are configured from the DXA hip images, and wherein in the step of processing the bone images, a preprocessing process for extracting texture features is performed with respect to the four regions of interest.

13. The computer reading medium of claim 12, wherein the preprocessing process is performed by a process of masking the regions of interest in different colors for each region along generated guidance lines, removing the guidance lines, and then improving a substrate pattern through contrast-limited adaptive histogram equalization and median filtering.

14. The computer reading medium of claim 9, wherein the development set is provided as a development set in which a case group and a control group are matched at 1:A from a case group data base and a control group data base and a final development set is provided by removing unusable bone images from the matched development set.

15. The computer reading medium of claim 9, wherein the optimal texture features include GLRLM (Gray Level Run Length Matrix) Run Entropy, GLRLM GLNN (Gray Level Non-uniformity Normalized), GLCM (Grey Level Co-occurrence Matrix) IMC1 (Information Measure of Correlation 1), GLCM IDMN (Inverse Difference Moment Normalized), GLCM Cluster Prominence, GLSZM SZN(Size-Zone Non-Uniformity), GLSZM (Gray Level Size Zone Matrix) SAHGLE (Small Area High Gray Level Emphasis), GLSZM (Gray Level Size Zone Matrix) GLN (Gray Level Non-Uniformity), GLSZM GLV (Gray Level Variance), and GLDM (Gray Level Dependence Matrix) DNN (Dependence Non-Uniformity Normalized).

16. The computer reading medium of claim 9, wherein the bone image is a dual energy X-ray absorptiometry (DXA) image, and
   a step of predicting the DXA image to be tested as a high-risk group when the bone radiomics score is more than a predetermined threshold is further performed, as a step of predicting whether there is fracture risk or the degree of fracture risk using the bone radiomics score model.

* * * * *